US009880152B2

(12) United States Patent
Gomez-Lopez et al.

(10) Patent No.: US 9,880,152 B2
(45) Date of Patent: Jan. 30, 2018

(54) LEUKOCYTE ACTIVATION AND METHODS OF USE THEREOF

(75) Inventors: Nardhy Gomez-Lopez, Edmonton (CA); David Olson, Edmonton (CA)

(73) Assignee: THE GOVERNORS OF THE UNIVERSITY OF ALBERTA, Edmonoton (CA)

( * ) Notice: Subject to any disclaimer, the term of this patent is extended or adjusted under 35 U.S.C. 154(b) by 230 days.

(21) Appl. No.: 13/980,544

(22) PCT Filed: Jan. 23, 2012

(86) PCT No.: PCT/CA2012/000068
§ 371 (c)(1),
(2), (4) Date: Sep. 21, 2013

(87) PCT Pub. No.: WO2012/097451
PCT Pub. Date: Jul. 26, 2012

(65) Prior Publication Data
US 2014/0011205 A1 Jan. 9, 2014

Related U.S. Application Data

(60) Provisional application No. 61/435,018, filed on Jan. 21, 2011.

(51) Int. Cl.
*G01N 33/50* (2006.01)
*G01N 33/68* (2006.01)
*C12Q 1/68* (2006.01)

(52) U.S. Cl.
CPC ....... *G01N 33/5047* (2013.01); *C12Q 1/6883* (2013.01); *G01N 33/6893* (2013.01); *C12Q 2600/158* (2013.01); *G01N 2800/368* (2013.01)

(58) Field of Classification Search
None
See application file for complete search history.

(56) References Cited

U.S. PATENT DOCUMENTS

2003/0134336 A1* 7/2003 Nebe .............................. 435/7.2

FOREIGN PATENT DOCUMENTS

WO 2012097451 A1 7/2012

OTHER PUBLICATIONS

Yuan et al., Leukocytes are primed in peripheral blood for activation during term and preterm labour, 2009, Molecular human reproduction 15(11): 713-724.*
Shah et al., Identification and quantification of preterm birth biomarkers in human cervicovaginal fluid by liquid chromatography/tandem mass spectrometry, 2009, Journal of Proteome Research 8(5): 2407-2417.*
Yuan, M., et al. "Leukocytes are primed in peripheral blood for activation during term and preterm labour." Molecular human reproduction 15.11 (2009): 713-724.*
Gomez-Lopez, N., et al. "Fetal membranes exhibit selective leukocyte chemotaxic activity during human labor." Journal of reproductive immunology 80.1 (2009): 122-131.*
Paris et al., Immune stress in late pregnant rats decreases length of gestation and fecundity, and alters later aognitive and affective behaviour of surviving pre-adolescent offspring. Stress. Nov. 2011;14(6):652-664.
Pate and Landis Keyes, Immune cells in the corpus luteum: friends or foes? Reproduction. Nov. 2001;122(5):665-676.
Pfaffl, A new mathematical model for relative quantification in real-time RT-PCR. Nucleic Acids Res. May 1, 2001;29(9);e45.
Ramos et al., Estrogen and progesterone modulation of eosinophilic infiltration of the rat uterine cervix. Steroids. Jul. 2000;65(7):409-414.
Risek et al., Modulation of Gap Junction Transcript and Protein Expression during Pregnancy in the Rat. J Cell Biol. Feb. 1990;110(2):269-282.
Shaikh, Estrone and estradiol levels in the ovarian venous blood from rats during the estrous cycle and pregnancy. Biol Reprod. Dec. 1971;5(3):297-307.
Shynlova et al., Monocyte chemoattractant protein-1 (CCL-2) integrates mechanical and endocrine signals that mediate term and preterm labor. J Immunol. Jul. 15, 2008;181(2)1470-1479.
Soloff et al., Oxytocin Receptors: Triggers for Parturition and Lactation? Science. Jun. 22, 1979;204(4399):1313-1315.
Springer, Traffic Signals for Lymphocyte Recirculation and Leukocyte Emigration: The Multistep Paradigm. Cell. Jan. 28, 1994;76(2):301-314.
Springer, Traffic Signals on Endothelium for Lymphocyte Recirculation and Leukocyte Emigration. Annu Rev Physiol. 1995;57:827-872.
Sugimoto et al., Failure of Parturition in Mice Lacking the Prostaglandin F Receptor. Science. Aug. 1, 1997;277(5326):681-683.
Tabiasco et al., Human Decidual NK Cells: Unique Phenotype and Functional Properties—A Review. Placenta. Apr. 2006;27 Suppl A:S34-39.
Tamassia et al., The MYD88-Independent Pathway Is Not Mobilized in Human Neutrophils Stimulated via TLR4. J Jmmunol. 2007;178:7344-7356.
Thomson et al., Leukocytes infiltrate the myometrium during human parturition: further evidence that labour is an inflammatory process. Hum Reprod. Jan. 1999;14(1):229-236.
Timmons et al., Cervical Remodeling during Pregnancy and Parturition. Trends Endocrinol Metab. Jun. 2010;21(6):353-361.
Timmons et al., Temporal Changes in Myeloid Cells in the Cervix during Pregnancy and Parturition. J Immunol. Mar. 1, 2009;182(5):2700-2707.
Vane et al., Cyclooxygenases 1 and 2. Annu Rev Pharmacol Toxicol. 1998;38:97-120.
Vargas et al., Comparison of the Proportions of Leukocytes in Early and Term Human Decidua. Am J Reprod Immunol. Apr. 1993;29(3):135-140.

(Continued)

*Primary Examiner* — Robert Yamasaki
(74) *Attorney, Agent, or Firm* — Acuity Law Group, PC; Michael A. Whittaker

(57) ABSTRACT

Described herein are compositions, methods and/or kits for determining the likelihood of a pregnant subject delivering at term, or developing a disorder associated with pregnancy. These compositions, methods and/or kits feature the measurement of the chemotactic activity of peripheral leukocytes, the measurement of ccl2 mRNA expression or the measurement of Fp or Otr protein expression.

6 Claims, 21 Drawing Sheets

(56) References Cited

OTHER PUBLICATIONS

Vega-Sanchez et al., Placental blood leukocytes are functional and phenotypically different than peripheral leukocytes during human labor. J Reprod Immunol. Jan. 2010;84(1):100-110.
Yellon et al., The Role of Leukocyte Traffic and Activation in Parturition. J Soc Gynecol Investig. Sep. 2003;10(6):323-338.
Young et al., Immunolocalization of Proinflammatory Cytokines in Myometrium, Cervix, and Fetal Membranes During Human Parturition at Term. Biol Reprod. Feb. 2002;66(2):445-449.
International Search Report issued in PCT/CA2012/000068 dated Apr. 5, 2012.
International Preliminary Report on Patentability issued in PCT/CA2012/000068 dated Aug. 1, 2013.
Abadia-Molina et al., Immune phenotype and cytotoxic activity of lymphocytes from human term decidua against trophoblast. J Reprod Immunol. Aug. 1996;31(1-2):109-123.
Albelda et al., Adhesion molecules and inflammatory injury. Faseb J. May 1994;8(8):504-512.
Arthur et al., Relationship between gene expression and function of uterotonic systems in the rat during gestation, uterine activation and both term and preterm labour. J Physiol. Dec. 15, 2008;586(Pt 24):6063-6076.
Bazer et al., Comparative aspects of implantation. Reproduction. Aug. 2009;138(2):195-209.
Birkedal-Hansen et al., Matrix Metalloproteinases: A Review. Crit Rev Oral Biol Med. 1993;4(2):197-250.
Blidaru et al., [Maternal immunophenotypic profile in normal pregnancy and preterm birth]. Rev Med Chir Soc Med Mat Iasi. Apr.-Jun. 2002;107(2):343-347.
Bokstrom et al., Leukocyte subpopulations in the human uterine cervical stroma at early and term pregnancy. Hum Reprod. Mar. 1997;12(3):586-590.
Bowen et al., Cytokines of the Placenta and Extra-placental Membranes: Roles and Regulation During Human Pregnancy and Parturition. Placenta. Apr. 2002;23(4):257-273.
Boyden, the Chemotactic Effect of Mixtures of Antibody and Antigen on Polymorphonuclear Leucocytes. J Exp Med. Mar. 1, 1962;115:453-466.
Bukovsky and Presl, Ovarian function and the immune system. Med Hypotheses. Apr. 1979;5(4):415-436.
Bulmer et al., Granulated lymphocytes in human endometrium: histochemical and immunohistochemical studies. Hum Reprod. Jul. 1991;6(6):791-798.
Butcher, Leukocyte-Endothelial Cell Recognition: Three (or More) Steps to Specificity and Diversity. Cell. Dec. 20, 1991;67(6):1033-1036.
Casatella, the production of cytokines by polymorphonuclear neutrophils. Immunol Today. Jan. 1995;16(1):21-26.
Challis et al., Endocrine and Paracrine Regulation of Birth at Term and Preterm. Endocr Rev. Oct. 2000;21(5):514-550.
Chen, Boyden Chamber Assay. Methods Mol Biol. 2005;294:15-22.
Chwalisz et al., Cervical ripening with the cytokines interleukin 8, interleukin 1β and tumour necrosis factor a in guinea-pigs. Hum Reprod. Nov. 1994;9(11):2173-2181.
Cook and Olson, The role of uterine prostaglandins in the initiation and maintenance of labour. Fetal and Maternal Medicine Review 1999;11:69-78.
Denucci et al., Rat Strain Differences in Susceptibility to Alcohol-Induced Chronic Liver Injury and Hepatic Insulin Resistance. Gastroenterol Res Pract. 2010;2010.
Dong et al., Differential Expression of Cyclooxygenase-1 and -2 Proteins in Rat Uterus and Cervix During the Estrous Cycle, Pregnancy, Labor and in Myometrial Cells. Prostaglandins. Jul. 1996;52(1):13-34.
Faraji et al., Stress precipitates functional deficits following striatal silent stroke: A synergistic effect. Exp Neurol. Dec. 2011;232(2):251-260.
Fuchs et al., Systemic and local regulation of oxytocin receptors in the rat uterus, and their functional significance. Can J Biochem Cell Biol. Jul. 1983;61(7):615-624.

Fuchs, Hormonal Control of Myometrial Function During Pregnancy and Parturition. Acta Endocrinol Suppl (Copenh). 1978;221:1-70.
Garfield et al., Gap junction formation in myometrium: control by estrogens, progesterone, and prostaglandins. Am J Physiol. Mar. 1980;238(3):C81-89.
Garfield et al., Gap Junctions: Their Presence and Necessity in Myometrium During Parturition. Science. Dec. 2, 1977;198(4320):958-960.
Gomez-Lopez et al., Chorion Exhibits Selective Leukocyte Chemotaxis by Secreting Specific Chemokines during Human Labor. Reproductive Sciences Mar. 2009;16(3)[Supplement]:69A-374A (Scientific Abstracts).
Gomez-Lopez et al., Changes in Leukocyte Subpopulations in the Choriodecidua and Fetal Membranes During Human Labor. Reproductive Sciences Jan. 2008;15(1)[Supplement]:86A Abstract #91.
Gomez-Lopez et al., Choriodecidua and amnion exhibit selective leukocyte chemotaxis during term human labor. Am J Obstet Gynecol. Apr. 2011;204(4):364.e9-16.
Gomez-Lopez et al., Differential Leukocyte Infiltration into Peri-Placental, Middle and Rupture Zones of the Human Fetal Membranes (FM) at Term Delivery: Association with Histology and Physiology. Reproductive Sciences Mar. 2010;17(3)[Supplement]:69A Abstract#10.
Gomez-Lopez et al., Invasion of the leukocytes into the fetal-maternal interface during pregnancy. J Leukoc Biol. Oct. 2010;88(4):625-633.
Gomez-Lopez et al., T Cell Recruitment and Contribution to an Inflammatory Microenvironment in the Choriodecidua During Human Labor. Reproductive Sciences Mar. 2010;17(3)[Supplement]:69A Abstract #8.
Gomez-Lopez et al., The Role of Chemokines in Term and Premature Rupture of the Fetal Membranes: A Review. Biol Reprod. May 2010;82(5):809-814.
Gorodeski et al., Myometrial Oxytocin Receptors Levels in the Pregnant Rat Are Higher in Distal than in Proximal Portions of the Horn and Correlate with Disparate Oxytocin Responsive Myometrial Contractility in these Segments. Endocrinology. Sep. 1990;127(3):1136-1143.
Helmig et al., Neutrophil elastase and secretory leukocyte protease inhibitor in prelabor rupture of membranes, parturition and intra-amniotic infectionJ Matern Fetal Neonatal Med. Oct. 2002;12(4):237-246.
Hirsch et al., Failure of E. coli bacteria to induce preterm delivery in the rat. J Negat Results Biomed. Jan. 4, 2009;8:1.
Hirst et al., Prostaglandin H Synthase-2 Expression Increases in Human Gestational Tissues with Spontaneous Labour Onset. Reprod Fertil Dev. 1995;7(3):633-637.
Hu et al., Differential distribution of interleukin-1alpha and interleukin-1 beta proteins in human placentas. J Reprod Immunol. Oct. 1992;22(3):257-268.
Hunt and Pollard, Macrophages in the Uterus and Placenta. Cuff Top Microbiol Immunol 1992;181:39-63.
Kelly, Inflammatory mediators and parturition. Rev Reprod. May 1996;1(2):89-96.
Laresgoiti-Servitje et al., An immunological insight into the origins of pre-eclampsia. Hum Reprod Update. Sep.-Oct. 2010;16(5):510-524.
Ley et al., Getting to the site of inflammation: the leukocyte adhesion cascade updated. Nat Rev Immunol. Sep. 2007;7(9):678-689.
Luo et al., Interleukin-8 Levels and Granulocyte Counts in Cervical Mucus During Pregnancy. Am J Reprod Immunol. Feb. 2000;43(2):78-84.
Lye et al., Increased Expression of Connexin-43 in the Rat Myometrium during Labor Is Associated with an Increase in the Plasma Estrogen:Progesterone Ratio. Endocrinology. Jun. 1993;132(6):2380-2386.
Viatsubara, Polymorphonuclear Leukocytes in the Fetal Membranes are Activated in Patients with Preterm Delivery: Ultrastructural and Enzyme-histochemical Evidence. Placenta. Mar.-Apr. 1999;20(2-3):185-188.

(56) References Cited

OTHER PUBLICATIONS

Viaymon et al., Human neutrophil collagenase (matrix metalloproteinase 8) in parturition, premature rupture of the membranes, and intrauterine infection. Am J Obstet Gynecol. Jul. 2000;183(1):94-99.

Mitchell et al., Intraperitoneal infusion of proinflammatory cytokines does not cause activation of the rat uterus during late gestation. Am J Physiol Endocrinol Metab. Oct. 2005;289(4):E658-664.

Norwitz et al., The Control of Labor. N Engl J Med. Aug. 26, 1999;341(9):660-666.

Olson et al., Control of Human Parturition. Semin Perinatol. Feb. 1995;19(1):52-63.

Osman et al., Leukocyte density and pro-inflammatory cytokine expression in human fetal membranes, decidua, cervix and myometrium before and during labour at term. Mol Hum Reprod. Jan. 2003;9(1):41-45.

Osman et al., Leukocyte Density and Proinflammatory Mediator Expression in Regional Human Fetal Membranes and Decidua Before and During Labor at Term. J Soc Gynecol Investig. Feb. 2006;13(2):97-103.

Osmers et al., Origin of cervical collagenase during parturition. Am J Obstet Gynecol. May 1992;166(5):1455-1460.

Gomez-Lopez et al., Chorion Exhibits Selective Leukocyte Chemotaxis by Secreting Specific Chemokines during Human Labor. Reprod Sci. Mar. 2009;16(3)(supplement):69A abstract 1.

Press and King, Distribution of Peroxidase and Granulocytes in the Human Uterus. Lab Invest. Feb. 1986;54 (2):188-203.

Abbas et al., Chapter 3: Leukocyte Migration into Tissues. Cellular and Molecular Immunology, 8th ed., 2012;280:37-53.

Gomez-Lopez et al., Chorion Exhibits Selective Leukocyte Chemotaxis by Secreting Specific Chemokines during Human Labor.Reprod Sci. Mar. 2009;16(3)(supplement):69A abstract 1.

Liggins, Cervical ripening as an inflammatory reaction. Discussed in the Cervix in Pregnancy and Labour, ed. in Ellwood D, Anderson, A. (Eds.), 1981:1-9.

Lye et al., The molecular basis of labour and tocolysis. Fetal Maternal Med Rev Aug. 1998;10(3):121-136.

Press and King, Distribution of Peroxidase and Granulocytes in the Human Uterus. Lab Invest. Feb. 1986;54(2):188-203.

Pritchard et al., The Placenta and Fetal Membranes and Matema I Adaptation to Pregnancy in Williams Obstetrics, Appleton Century Crofts, 1985, Stamford, CT., 3 pages.

\* cited by examiner

Median and SEM; Menn Whitney U $p$= 0.010[a]; 0.008[b]; 0.029[c]; 0.016[d]

Median and SEM; Mann Whitney U p= a0.019; b0.008; c0.029; d0.016

Median and SEM; Mann Whitney U p= a0.010; b0.008

Median and SEM; Menn Whitney U $p=$ 0.010[a]; 0.008[b]; 0.036[c]; 0.024[d]

Mean and SEM; Mann Whitney U p=a0.008; b0.016

FIGURE 7
Leukocyte Infiltration and Recruitment
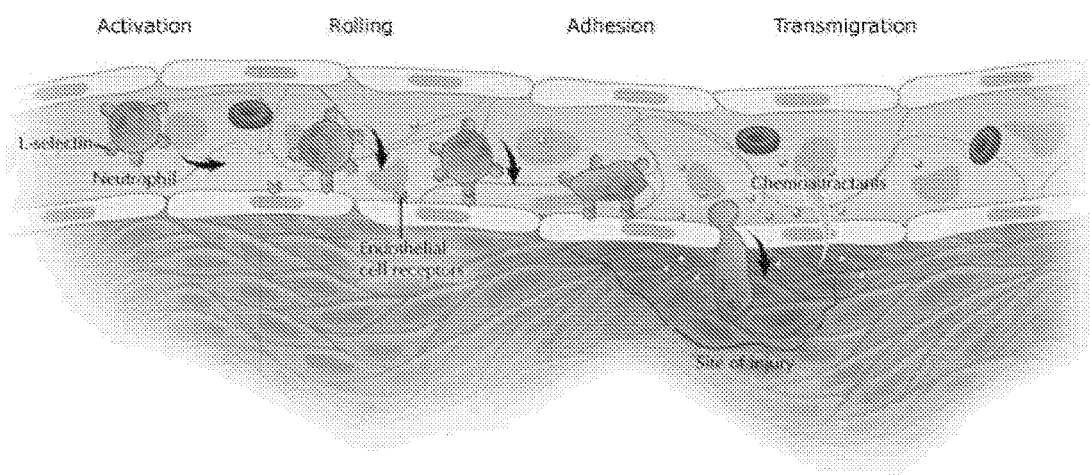
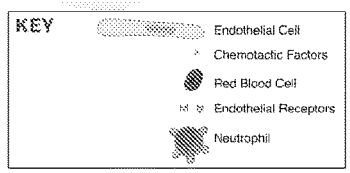
http://www.gluegrant.org/chemotaxis.html Fetal membranes exhibit leukocyte chemotactic activity Chemotactic activity is selective

| Leukocytes | % |
|---|---|
| T cells | 5.3 |
| B cells | 4.4 |
| Monocytes | 36.5 |
| NK cells | 4.5 |
| PMN | 3.0 |

FIGURE 11

Collection of Leukocytes

1. Blood (10 mL) is drawn from a peripheral vein of a pregnant woman
2. Blood is mixed with Polymorphoprep in tube
3. Tube is centrifuged
4. Leukocytes are collected and washed with PBS
5. Leukocytes are placed into Boyden Chamber

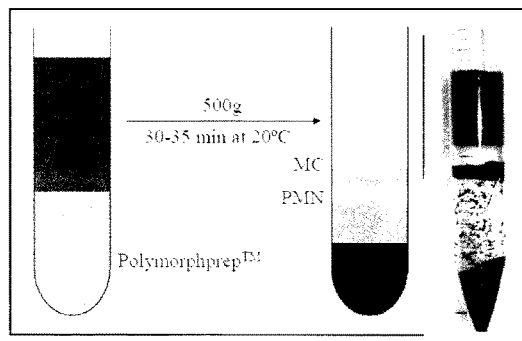

Figure 2: Purification of PMNs using Polymorphprep™ MC = mononuclear cells; PMNs = polymorphonuclear leukocytes. Inset right shows an actual separation in a 15 ml tube FIGURE 16
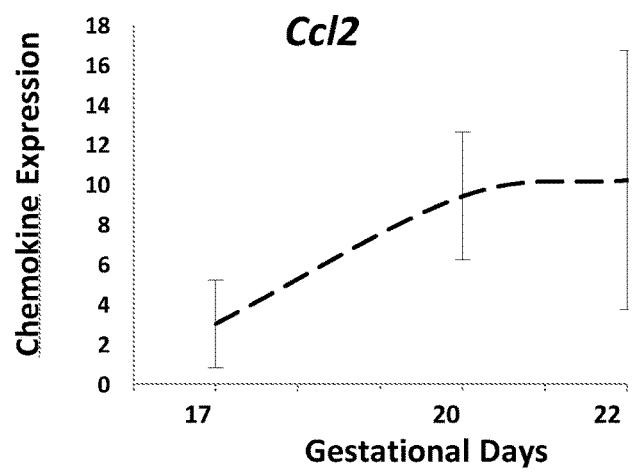
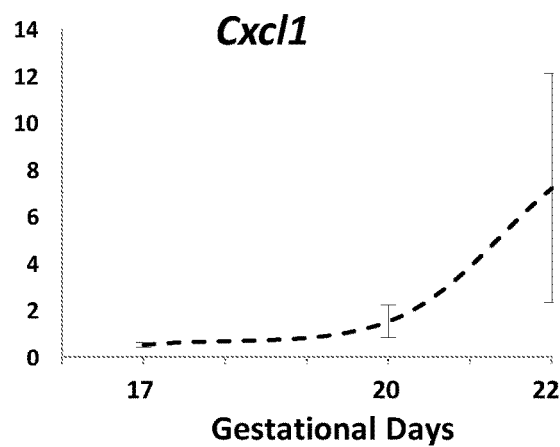
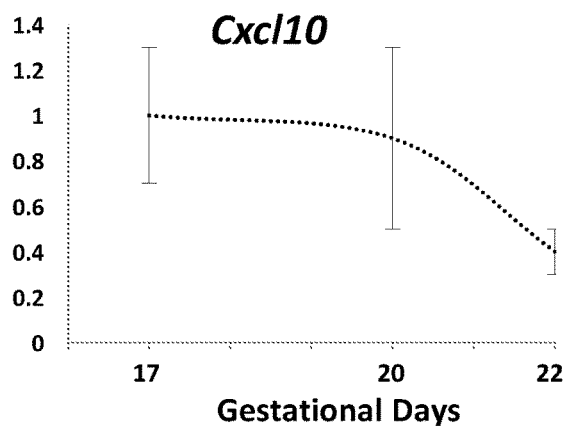

FIGURE 21

Table 1
Primers used for RT-PCR

| Gene | Primers | Optimal Temperature (°C) | NCBI Reference Sequences |
|---|---|---|---|
| Cxcl1 | f: 5'-gca CCC AAA CCG AAG TCA-3'<br>r: 5'-AAG CCA GCG TTC ACC AGA-3' | 60 | NM_030845 |
| Cxcl10 | f: 5'- GGT GAG CCA AAG AAG GTC-3'<br>r: 3'-ACA CTG GGT AAA GGG AGG-3' | 60 | NM_139089.1 |
| Ccl2 | f: 5'-GCA GGT GTC CCA AAG AAG-3'<br>r: 3'-TCA AAG GTC CTG AAG TCC-3' | 60 | NM_031530 |
| Fp | f: 5'-CTGGCCATAATGTGCGTCTC-3'<br>r: 5'-TGTCGTTTCACAGGTCACTGG-3' | 60 | NM-013115.1 |
| Ocr | f: 5'-CGATTGCTGGGCGGTCTT-3'<br>r: 5'-CCGCCGCTGCCGTCTTGA-3' | 62 | NM-012871.2 |
| Cyp | f: 5'-CACCGTGTTCTTCGACATCAC-3'<br>r: 5'-CCAGTGCTCAGAGCTCGAAAG-3' | 60 | NM-017101 |

LEUKOCYTE ACTIVATION AND METHODS OF USE THEREOF

RELATED APPLICATIONS

The present invention is filed under 35 U.S.C. § 371 as the U.S. national phase of International Application No. PCT/CA2012/000068, filed Jan. 23, 2012, which designated the U.S. and claims the benefit of priority to U.S. Provisional Patent Application No. 61/435,018 filed Jan. 21, 2011, which is hereby incorporated by reference in its entirety including all tables, figures, and claims.

FIELD OF THE INVENTION

The field of the invention generally relates to compositions, methods and kits for compositions, methods and/or kits for determining the likelihood of developing a disorder of pregnancy, such as preterm delivery.

BACKGROUND OF THE INVENTION

The process of normal labor in humans represents a type of inflammatory response. Many of the cellular and biochemical mediators of inflammation elicit specific responses in the quiescent uterus, the cervix and the fetal membranes[1]. As part of this process, leukocytes infiltrate the myometrium[2], the cervix[3] and the fetal membranes[3,4]. These leukocytes, along with the resident cells of the reproductive tissues secrete inflammatory mediators including cytokines, matrix metalloproteinases (MMPs), and prostaglandins (PGs), which participate in the regulation of the events of labor[1,5].

It has been proposed that specific leukocyte subsets infiltrate the fetal membranes around the time of labor, creating an inflammatory microenvironment and secreting mediators which may allow the final rupture of these tissues[3,6]. Regarding to the phenotype of the infiltrated leukocytes in the fetal membranes before and at the parturition time, it has been reported that they generally consisting of granulocytes, T cells and a lesser proportion of monocytes.

Leukocyte recruitment and homing are regulated by specific mediators and generally occur in sequential steps. First, tissues secrete chemokines which are the soluble mediators that are responsible for the selective recruitment of leukocytes to a particular tissue[8]. Once they have arrived at the tissue, leukocytes express cell adhesion molecules (CAMs) which allow them to adhere to the vascular endothelium and subsequently to extravasate from the blood vessel and into the tissue[9]. In the reproductive tissues, it has been demonstrated that chemokines recruit specific leukocyte subsets before and during labor[6,10].

Preterm delivery is the largest contributor to perinatal mortality and morbidity with long term consequences and tremendous personal and societal costs. In Alberta, the preterm birth rate is >9%, and in the USA it is >12%, of all pregnancies.

Currently, the best predictor of preterm birth is considered to be whether the mother has had a previous preterm pregnancy. A mother has approximately a 15% chance of delivering the next baby preterm as well. If the mother has had two previous preterm pregnancies, the predictability for the current pregnancy doubles to about 30%.

If a mother was preterm herself, or if her first or second degree relatives had preterm births, the risk of preterm birth is increased.

Twin studies estimate an overall heritability from 15% to 40%.

Presently, there is no reliable test of any kind that predicts women at risk of preterm delivery.

The only pregnancy test on the market is the fetal fibronectin test from Hologic in which a cervical swab can be tested for the presence of fetal fibronectin. This is used as a test to predict pregnancy maintenance and does not predict preterm birth or pregnancy termination. It selects for the women not to treat, but does not select for those who should be treated.

It is, therefore, desirable to provide compositions, methods and/or kits for determining the likelihood of developing a disorder of pregnancy, such as preterm delivery.

This background information is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

In accordance with one aspect of the present invention, there is provided a method for determining the likelihood of a pregnant subject undergoing term delivery, comprising: obtaining peripheral leukocytes from said pregnant subject; and determining a chemotactic activity of said leukocytes, wherein an increased likelihood of term delivery is indicated when said chemotactic activity of said leukocytes is at a level characteristic of a full term pregnancy.

In accordance with one aspect of the present invention, there is provided a method for determining the likelihood of a pregnant subject undergoing preterm delivery, comprising: obtaining peripheral leukocytes from said pregnant subject prior to about week 37 of pregnancy; and determining a chemotactic activity of said leukocytes, wherein an increased likelihood of preterm delivery is indicated when said chemotactic activity of said leukocytes is at a level characteristic of a full term pregnancy.

In accordance with one aspect of the present invention, there is provided a method for determining the likelihood of a pregnant subject developing a disorder associated with pregnancy, comprising: obtaining peripheral leukocytes from said pregnant subject prior to about week 37 of pregnancy; and determining a chemotactic activity of said leukocytes, wherein an increased likelihood of developing said disorder associated with pregnancy is indicated when said chemotactic activity of said leukocytes is at a level characteristic of a full term pregnancy.

In a specific aspect, said disorder associated with pregnancy is preterm delivery, preeclampsia, preterm premature rupture of membranes, or placental abruption.

In a specific aspect, determining said chemotactic activity comprises measuring migration of said leukocytes towards a chemoattractant.

In a specific aspect, said chemoattractant is a factor present in a sample comprising choriodecidua extract, or fetal membrane extract, wherein each said extract is obtained from a full term pregnancy subject.

In a specific aspect, said chemoattractant comprises a factor present within a sample comprising a uterine extract or a cervical extract; wherein each said extract is obtained from a full term pregnancy subject.

In a specific aspect, said uterine extract comprises an upper uterine extract, a middle uterine extract, a lower uterine extract, or a cervical extract.

In a specific aspect, said leukocyte is a granulocyte, T-lymphocyte, monocyte, NK cell, or B-lymphocyte.

In accordance with one aspect of the present invention, there is provided a method for determining the likelihood of a pregnant subject undergoing term delivery, comprising: obtaining a sample from a pregnant subject, contacting the sample with a reagent to a biomarker, to form a complex between the agent and the biomarker present in the sample; measuring the complex formed to determine the amount or concentration of said biomarker in the sample; wherein an increased likelihood of term delivery is indicated when said biomarker is at a level characteristic of a full term pregnancy.

In accordance with one aspect of the present invention, there is provided a method for determining the likelihood of a pregnant subject undergoing preterm delivery, comprising: obtaining a sample from a pregnant subject prior to about week 37 of pregnancy; contacting the sample with a reagent to a biomarker, to form a complex between the agent and the biomarker present in the sample; measuring the complex formed to determine the amount or concentration of said biomarker in the sample; wherein an increased likelihood of preterm delivery is indicated when said biomarker is at a level characteristic of a full term pregnancy.

In accordance with one aspect of the present invention, there is provided a method for determining the likelihood of a pregnant subject developing a disorder associated with pregnancy, comprising: obtaining a sample from a pregnant subject prior to about week 37 of pregnancy, contacting the sample with a reagent to a biomarker, to form a complex between the agent and the biomarker present in the sample; measuring the complex formed to determine the amount or concentration of said biomarker in the sample; wherein an increased likelihood of developing said disorder associated with pregnancy is indicated when said biomarker is at a level characteristic of a full term pregnancy.

In a specific aspect, said biomarker comprises a protein, a gene, or a mRNA.

In a specific aspect, said mRNA comprises ccl2 mRNA.

In a specific aspect, said sample comprises leukocytes.

In a specific aspect, said sample comprises an upper uterine extract, a middle uterine extract, a lower uterine extract, a fetal membrane extract, or a placental extract.

In a specific aspect, said protein comprises a uterine activation protein (UAP).

In a specific aspect, said UAP comprises Fp and said sample comprises an upper uterine extract.

In a specific aspect, said UAP comprises Otr and said sample comprises an upper uterine extract, a middle uterine extract, or a lower uterine extract.

In a specific aspect, said subject is a human.

In accordance with one aspect of the present invention, there is provided a kit for determining the likelihood of a pregnant subject undergoing term delivery, comprising: a reagent for determining a chemotactic activity of leukocytes from said pregnant subject; and instructions for the use thereof, wherein an increased likelihood of term delivery is indicated when said chemotactic activity of said leukocytes is at a level characteristic of a full term pregnancy.

In accordance with one aspect of the present invention, there is provided a kit for determining the likelihood of a pregnant subject undergoing preterm delivery, comprising: a reagent for determining a chemotactic activity of leukocytes from a pregnant subject prior to about week 37 of pregnancy; and instructions for this use thereof, wherein an increased likelihood of preterm delivery is indicated when said chemotactic activity of said leukocytes is at a level characteristic of a full term pregnancy.

In accordance with one aspect of the present invention, there is provided a kit for determining the likelihood of a pregnant subject developing a disorder associated with pregnancy, comprising: a reagent for determining a chemotactic activity of leukocytes from a pregnant subject prior to about week 37 of pregnancy; and instructions for the use thereof, wherein an increased likelihood of developing said disorder associated with pregnancy is indicated when said chemotactic activity of said leukocytes is at a level characteristic of a full term pregnancy.

In a specific aspect, said disorder associated with pregnancy is preterm delivery, preeclampsia, preterm premature rupture of membranes, or placental abruption.

In a specific aspect, determining said chemotactic activity comprises measuring migration of said leukocytes towards said reagent, wherein said reagent comprises a chemoattractant.

In a specific aspect, said chemoattractant is a factor present in a sample comprising choriodecidua extract, or fetal membrane extract, wherein each said extract is obtained from a full term pregnancy subject.

In a specific aspect, said chemoattractant comprises a factor present within a sample comprising a uterine extract or a cervical extract; wherein each said extract is obtained from a full term pregnancy subject.

In a specific aspect, said uterine extract comprises an upper uterine extract, a middle uterine extract, a lower uterine extract, or a cervical extract.

In a specific aspect, said leukocyte is a granulocyte, T-lymphocyte, monocyte, NK cell, or B-lymphocyte.

In accordance with one aspect of the present invention, there is provided a kit for determining the likelihood of a pregnant subject undergoing term delivery, comprising: a reagent for measuring the amount or concentration of a biomarker in a sample a pregnant subject; and instructions for the use thereof, wherein an increased likelihood of term delivery is indicated when said biomarker is at a level characteristic of a full term pregnancy.

In accordance with one aspect of the present invention, there is provided a kit for determining the likelihood of a pregnant subject undergoing preterm delivery, comprising: a reagent for measuring the amount or concentration of a biomarker in a sample from a pregnant subject prior to about week 37 of pregnancy; and instructions for the use thereof, wherein an increased likelihood of preterm delivery is indicated when said biomarker is at a level characteristic of a full term pregnancy.

In accordance with one aspect of the present invention, there is provided a kit for determining the likelihood of a pregnant subject developing a disorder associated with pregnancy, comprising: a reagent for measuring the amount or concentration of a biomarker in a sample from a pregnant subject prior to about week 37 or pregnancy, wherein an increased likelihood of developing said disorder associated with pregnancy is indicated when said biomarker is at a level characteristic of a full term pregnancy.

In a specific aspect, said biomarker comprises a protein, a gene, or a mRNA.

In a specific aspect, said mRNA comprises ccl2 mRNA.

In a specific aspect, said sample comprises leukocytes.

In a specific aspect, said sample comprises an upper uterine extract, a middle uterine extract, a lower uterine extract, a fetal membrane extract, or a placental extract.

In a specific aspect, said protein comprises a uterine activation protein (UAP).

In a specific aspect, said UAP comprises Fp and said sample comprises an upper uterine extract.

In a specific aspect, said UAP comprises Otr and said sample comprises an upper uterine extract, a middle uterine extract, or a lower uterine extract.

In a specific aspect, said subject is a human.

BRIEF DESCRIPTION OF THE DRAWINGS

Embodiments of the present invention will now be described, by way of example only, with reference to the attached Figures, wherein:

FIG. 7 is a representation of the process of normal leukocyte activation, recruitment and infiltration. Leukocytes activated in response to chemotactic factors must squeeze through junctions between endothelial cells to invade or infiltrate underlying tissues.

FIG. 11 is a representation of the collection of leukocytes.

FIG. 16. Chemokine expression in peripheral leukocytes. Panel A, relative expression of ccl2 in total peripheral leukocyte population; Panel B, relative expression of cxcl1 in total peripheral leukocyte population; and panel C, relative expression of cxcl10 in total peripheral leukocyte population. Data shown are means±SEM of determinations in duplicate per group (n=5 each). Means with different letters are significantly different.

FIG. 21. Depicts a Table of primers used for RT-PCR.

Figure 1:
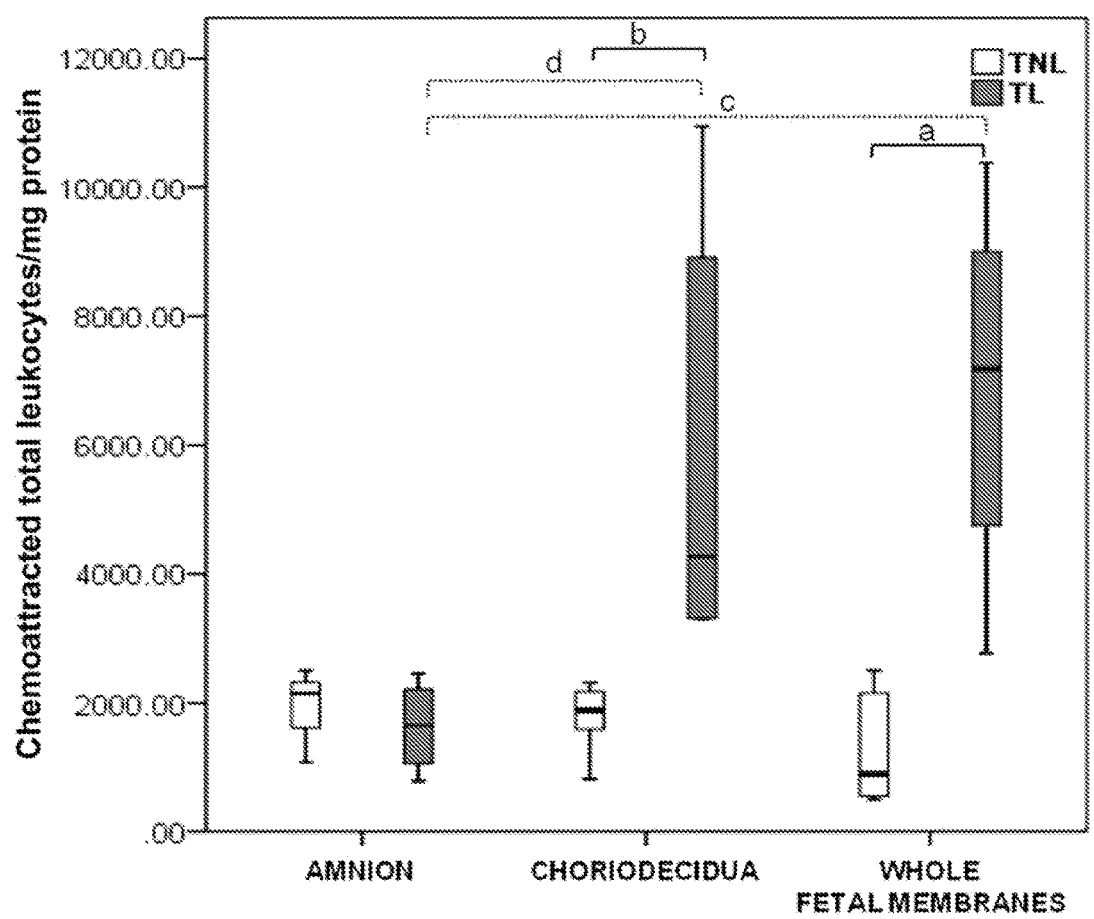
FIG. 1 is a graph depicting total leukocyte chemotactic activity. Black bars represent women who underwent labor at term (TL) and white bars represent women who did not undergo labor and were delivered at term by cesarean section (TNL). The whole fetal membranes and choriodecidua extracts from TL chemoattracted more leukocytes than those extracts from TNL (p=a0.010; b0.008). In TL tissues, the whole fetal membranes and choriodecidua extracts showed more leukocyte chemotactic activity than the amnion extracts (p=c0.029; d0.016). Data are presented as mean±SEM of chemoattracted leukocytes by each extract, from five different women per group, in triplicate.

In the Detailed Description that follows, the numbers in bold face type serve to identify the component parts that are described and referred to in relation to the drawings depicting various embodiments of the invention. It should be noted that in describing various embodiments of the present invention, the same reference numerals have been used to identify the same of similar elements. Moreover, for the sake of simplicity, parts have been omitted from some figures of the drawings.

DETAILED DESCRIPTION

As will be described in more detail below, one aspect of the present invention relates to compositions, methods and/or kits for identifying the phenotype of leukocytes chemoattracted to a biological sample from a subject.

Also as will be described in more detail below, one aspect of the present invention relates to compositions, methods and/or kits for determining the likelihood a pregnant subject undergoing term delivery, and of a developing a pregnancy-associated disorder.

In one example, there is provided a method for determining the likelihood of a pregnant subject undergoing term delivery, comprising: obtaining peripheral leukocytes from said pregnant subject; and determining a chemotactic activity of said leukocytes, wherein an increased likelihood of term delivery is indicated when said chemotactic activity of said leukocytes is at a level characteristic of a full term pregnancy.

In one example, there is provided a method for determining the likelihood of a pregnant subject undergoing preterm delivery, comprising: obtaining peripheral leukocytes from said pregnant subject prior to about week 37 of pregnancy; and determining a chemotactic activity of said leukocytes, wherein an increased likelihood of preterm delivery is indicated when said chemotactic activity of said leukocytes is at a level characteristic of a full term pregnancy.

In one example, there is provided a method for determining the likelihood of a pregnant subject developing a disorder associated with pregnancy, comprising: obtaining peripheral leukocytes from said pregnant subject prior to about week 37 of pregnancy; and determining a chemotactic activity of said leukocytes, wherein an increased likelihood of developing said disorder associated with pregnancy is indicated when said chemotactic activity of said leukocytes is at a level characteristic of a full term pregnancy.

The term "subject" or "patient" or "individual", as used herein, refers to a eukaryote. A biological sample is typically obtained from a eukaryotic organism including, but not limited to, mammals. Mammalian subjects include, but are not limited to, primates such as a human; non-human primates including chimpanzees and the like; livestock, including but not limited to, cows sheep, pigs, and the like; companion animals, including but not limited to, dogs, cats, horses, rabbits, rodents including mice and rats, and the like.

In a specific example, the subject is a pregnant female human.

In another specific example, the subject is a pregnant female rat.

The term "sample" or "biological sample" as used herein, encompasses a variety of cells, cell-containing bodily fluids and/or secretions as well as tissues including, but not limited to a cell(s), tissue, whole blood, blood-derived cells, plasma, serum, sputum, mucous, bodily discharge, and combinations thereof, and the like. Biological samples may include, but are not limited to, tissue and/or fluid isolated from a subject. Biological samples may also include sections of tissues such as biopsy and autopsy samples, formalin-fixed paraffin-embedded (FFPE) samples, frozen sections taken for histologic purposes, blood and blood fractions or products (e.g., serum, plasma, platelets, red blood cells, white blood cells and the like), sputum, stool, tears, mucus, hair, and skin. Biological samples also include explants and primary and/or transformed cell cultures derived from animal or patient tissues. Biological sample also include fetal membranes, including fetal membranes obtained fragments from the amnion, choriodecidua and whole fetal membranes.

In certain examples, biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, or secretions from the breast.

In a specific example, a biological sample is a blood samples, or a blood fraction.

In another specific example, a biological sample comprises cervical or uterine samples.

A biological sample may be obtained using those methods known to the skilled worker. Methods of obtaining such samples from a subject are known to the skilled worker.

As used herein, "obtaining a sample" or "obtaining a biological sample" refers to such methods as will be well known to the skilled worker. A biological sample may be obtained directly or indirectly from the subject. The term "obtaining" a biological sample may comprise receiving a biological sample from an agent acting on behalf of the subject. For example, receiving a biological sample from a doctor, nurse, hospital, medical center, etc., either directly or indirectly, e.g. via a courier or postal service. In some cases the biological sample is obtained from archival repositories. In one example, the methods of the invention are carried out in vitro or ex vivo.

For example, a blood sample, such as a peripheral blood sample, may be collected using venipuncture.

A biological sample may be obtained by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

A biological sample can be collected on more than one occasion.

In some examples, a tissue sample may be obtained from a biopsy.

The term "biopsy", as used herein, refers to the process of removing a tissue sample for the methods described herein, and to the tissue specimen itself. Any biopsy technique known in the art can be applied to the methods of the present invention. The biopsy technique applied will depend on the tissue type to be evaluated, the size and type biopsy, among other factors. Representative biopsy techniques include, but are not limited to, excisional biopsy, incisional biopsy, needle biopsy and surgical biopsy. A biopsy may be a "core-needle biopsy", or a "fine-needle aspiration biopsy" which generally obtains a suspension of cells from within a target tissue. In the case of placental tissue, biopsies may be conducted pre- or post-delivery. Additional examples include gross apportioning of a mass, microdissection, laser-based microdissection, or other art-known cell-separation methods.

In one example, a biological sample is assessed for leukocyte chemotactic activity, and the number and phenotype of the chemoattracted leukocytes are characterized. Methods of measuring chemotaxis are known, and include the use of a Boyden chamber.

The term "leukocyte" or "white blood cell", as used herein, refers to any type of white blood cell. Leukocytes may be peripheral leukocytes. Leukocytes include adaptive immune cells and innate immune cells. The term "adaptive immune cells" (or "memory immune cells") and "innate immune cells" as used herein have their conventional meaning. Examples of leukocytes include, for example granulocytes (e.g., neutrophils, eosinophils, basophils), mononuclear phagocytes, and lymphocytes (e.g., B cells, T cells, natural killer (NK) cells).

Leukocytes may be isolated in accordance with any suitable technique. In once example, leukocytes are isolated from peripheral blood using Polymorphprep™.

Leukocytes may be sorted into particular subcategories or types in accordance with any suitable technique.

The term "Boyden chamber", as used herein, encompasses generically any instrument used to study chemotaxis (also referred to as chemotactic activity), and in particular trans-membrane chemotaxis. It is also referred to as "trans-well migration" or an in vitro cell migration assay.

The Boyden chamber, is based on a chamber of two medium-filled compartments separated by a microporous membrane. In general, cells are placed in the upper compartment and are allowed to migrate through the pores of the membrane into the lower compartment, in which chemotactic agents are present. After an appropriate incubation time, the number of cells that have migrated to the lower side of the membrane is determined. The Boyden chamber-based cell migration assay has also been called filter membrane migration assay, trans-well migration assay, or chemotaxis assay. A number of different Boyden chamber devices are available commercially, as is well known to the skilled worker. Alternate Boyden chambers may be based on or employ a Boyden chamber whereby the separation of the two (migratory cells- and chemottractant-containing) units is accomplished not only by a membrane but by cell-coated membranes. The filter membranes may be made from a variety of materials, including, but not limited to polycarbonate, polysulfone, polyvinyl or polystyrene.

The pore size of the membranes selected on the basis of its intended use, and may be in the range for from about 0.5 to about 10 µm diameter, desirably from about 2.5 to about 7.5 µm, or desirably about 5 µm. In a specific example, in the case of leukocytes, the pore size is about 5 µm.

The term "chemoattractant", as used herein, refers to a molecule which gives rise to the migration of certain target cells by establishing a chemotactic gradient along which the target cells can move. Examples of chemoattractants include, but are not limited to, a protein(s). Once example of a chemoattractant is a chemokine. Chemoattractants may be present in cell and/or tissue extracts.

In a specific example, the biological sample is amnion, choriodecidua or whole fetal membrane extracts obtained from pregnant humane females at term, with or without labour were assessed for leukocyte chemotactic activity, and the number and phenotype of the chemoattracted leukocytes were characterized by flow cytometry.

In this specific example, all of the extracts exhibited chemotactic activity with more leukocytes chemoattracted by the choriodecidua and the whole fetal membranes during labor compare with no labor (p=0.010, 0.008).

As noted above, one aspect of the present invention relates to compositions, methods and/or kits for predicting or determining the likelihood of a pregnancy-associated disorder in a subject, for example, which is higher than in a control group, such as a normal pregnancy control.

The term "normal pregnancy" as used herein refers to a pregnancy the proceeds to term without any complications, and is also referred to as a term pregnancy or full term pregnancy. Typically, a normal pregnancy is a pregnancy without a pregnancy-associated disorder.

As used herein, the term "term pregnancy" and "full term pregnancy" refers to the onset of labour after the $37^{th}$ week or gestation, in humans. In another example, these terms refer to the onset of labour between about the $37^{th}$ week and $40^{th}$ week of gestation.

The term "pregnancy-associated disorder", as used herein, refers to any condition or disease that may affect a pregnant woman, the fetus the woman is carrying, or both the woman and the fetus. Such a condition or disease may manifest its symptoms during a limited time period, e.g., during pregnancy or delivery, or may last the entire life span of the fetus following its birth. Non-limited examples of pregnancy-associated disorders include preterm labor, preeclampsia, preterm premature rupture of membranes, placental abruption, ectopic pregnancy, fetal chromosomal abnormalities, hypertensive disorders with or without associated proteinuria, chronic hypertension, gestational hypertension (pregnancy induced hypertension (PIH)), and the like.

In one example, a pregnancy-associated disorder is preterm labor (also referred to as preterm delivery), preeclampsia, preterm premature rupture of membranes and/or placental abruption.

In a specific example, the pregnancy-associated disorder is preterm labor.

The terms "preterm labour" and "premature labour" and "preterm delivery", as used herein, refers to the premature onset of labor resulting in expulsion from the uterus of a viable infant before the normal end of gestation (i.e. preterm birth or delivery), if not treated. In a specific example, in the case of humans, preterm labour refers to the onset of labor with effacement and dilation of the cervix before the 37th week of gestation. In another example, preterm labour refers to the onset of labor with effacement and dilation of the cervix between about the 20$^{th}$ week of gestation and the 37th week of gestation.

Preterm labour may or may not be associated with vaginal bleeding or rupture of membranes. Preterm labor may or may not be related to factors including without limitation infection (eg, bacterial vaginosis [BV], sexually transmitted diseases [STDs], urinary tract infections, chorioamnionitis), uterine distention (eg, multiple gestation, polyhydramnios), uterine distortion (eg, müllerian duct abnormalities, fibroid uterus), compromised structural support of the cervix (eg, incompetent cervix, previous cone biopsy or loop electrosurgical excision procedure [LEEP]), abruptio placentae, uteroplacental insufficiency (eg, hypertension, insulin-dependent diabetes, drug abuse, smoking, alcohol consumption), stress either indirectly by associated risk behaviors or by direct mechanisms including fetal stress.

The term "preeclampsia", as used herein, refers to a condition that occurs during pregnancy, the main symptom of which is various forms of high blood pressure often accompanied by the presence of proteins in the urine and edema (swelling). Preeclampsia, sometimes called toxemia of pregnancy, is related to a more serious disorder called "eclampsia," which is preeclampsia together with seizures. These conditions usually develop during the second half of pregnancy (after 20 weeks), though they may develop shortly after birth or before 20 weeks of pregnancy.

The term "placental abruption" as sued herein, refers to a condition that occurs during and may be associated with hypertension, diabetes, a multiply pregnancy, an unusually large amount of amniotic fluid, numerous previous deliveries, or advanced maternal age The term "treatment" or "treated", as used herein, refers to both therapeutic treatment and prophylactic or preventative measures, wherein the object is to prevent or slow down (lessen) the targeted condition or disorder. Those in need of treatment include those already with the disorder as well as those prone to have the disorder or those in whom the disorder is to be prevented.

Treatment for pregnancy-associated disorders are known to the skilled worker.

In some examples, a suitable treatment or medicament is administered for treatment of the pregnancy associated hypertensive disorder, and may for example be selected from aldomet, labatolol, hydralazine, nifedipine (Procardia, Adalat), diuretics, clonidine, calcium channel blockers, vasodilators, magnesium sulphate (MgSO4), and combinations thereof.

In other examples, tocolytic agents that may be utilized in methods as described herein may for example be selected from MgSO4, nifedipine, fenoterol, ritodrine (Yutopar), atosiban, salbutamol, indomethacin, terbutaline (Brethine), oxytocin antagonists, and combinations thereof.

In other examples, steroids that may be used for promoting maturation of foetal lungs include corticosteroids and glucocorticoids (such as betamethasone, dexamethasone, and hydrocortisone).

The term "prediction" and "determination in the likelihood" as used herein, refers to providing a measure of relative risk for developing a pregnancy-associated disorder in a patient. As used herein, the term "providing a prognosis" refers to providing a prediction of the probable course and outcome of a pregnancy-associated disorder.

As used herein, the term "diagnosis" refers to detecting a pregnancy-associated disorder or a risk or propensity for development a pregnancy-associated disorder. It will be appreciated that typically any method of diagnosis includes false positives and false negatives. Accordingly, it is typical that a method of diagnosis does not necessarily provide 100% accuracy.

In one example, a determination of the likelihood of a disorder associated with pregnancy is made by measuring chemotaxis of leukocytes, obtained from a pregnant human female, towards a chemoattractant.

In a specific example, the chemoattractant is a protein extract of term chorio-decidual tissue and chemotaxis is measured using a Boyden chamber. If a larger-than-normal number of leukocytes have migrated for a particular gestational age, the risk of having preterm labour will be increased. As demonstrated in the Examples, leukocytes become more activated as pregnancy progresses, i.e. responsive in terms of migratory activity to a standard dose of chemotactic factor. Activated leukocytes responding to a chemotactic signal from intrauterine fetal/maternal tissues attract the leukocytes. The degree of activation increases as delivery nears. A patient identified with a likelihood of preterm labour may receive appropriate treatment, as would be known to the skilled worker.

In a specific example, a determination of the likelihood of a disorder associated with pregnancy is undertaken as follows. Whole blood (e.g., 10 mL) from a pregnant human female, obtained from a routine blood sampling taken during a prenatal visit or at a visit to a clinic, is mixed with 10 mL Polymorphoprep™ (a commercial product that helps separate the leukocytes). The blood and Polymorphoprep™ are centrifuged for 30 min to isolate the leukocytes. The leukocytes are placed into one well of a modified Boyden chamber. Into the other well of the Boyden chamber is placed a chemotactic protein extract of term chorio-decidual tissue. The chamber is incubated for 2.0 hours, after which the number and type of leukocytes that have migrated from the leukocyte chamber to the chemotaxis chamber are assessed by flow cytometry. If a larger-than-normal number of leukocytes (for example granuloctyes, B and T lymphocytes and monocytes/macrophages) have migrated for that particular gestational age, the risk of having preterm labour will be increased. The principle behind the test is that we have just demonstrated in pregnant rats with this technique that leukocytes become more 'activated' as pregnancy progresses, i.e. responsive in terms of migratory activity to a standard dose of chemotactic factor. In order to move from one chamber to the other within a Boyden chamber, the leukocytes must pass through pores with a diameter of about 5 µm, whereas typically they have diameters ranging from 8-14 µm. Only activated leukocytes responding to a chemotactic signal from intrauterine fetal/maternal tissues will attract the leukocytes. As shown herein, the degree of activation increases as delivery nears.

In accordance with another aspect of the present invention, there is provided a method of monitoring the responsiveness to treatment for disorder associated with pregnancy.

In another embodiment, a method as described herein comprises qualitatively or quantitatively determining, analyzing or measuring a biological sample from a subject for the presence or absence, or amount or concentration, of one or more biomarkers associated with the diagnosis and/or prognosis and/or therapeutic monitoring of pregnancy and/ or a disorder associated with pregnancy.

In one example there is provided a method for determining the likelihood of a pregnant subject undergoing term delivery, comprising: obtaining a sample from a pregnant subject, contacting the sample with a reagent to a biomarker, to form a complex between the agent and the biomarker present in the sample; measuring the complex formed to determine the amount or concentration of said biomarker in the sample; wherein an increased likelihood of term delivery is indicated when said biomarker is at a level characteristic of a full term pregnancy.

In one example there is provided a method for determining the likelihood of a pregnant subject undergoing preterm delivery, comprising: obtaining a sample from a pregnant subject prior to about week 37 of pregnancy; contacting the sample with a reagent to a biomarker, to form a complex between the agent and the biomarker present in the sample; measuring the complex formed to determine the amount or concentration of said biomarker in the sample; wherein an increased likelihood of preterm delivery is indicated when said biomarker is at a level characteristic of a full term pregnancy.

In one example there is provided a method for determining the likelihood of a pregnant subject developing a disorder associated with pregnancy, comprising: obtaining a sample from a pregnant subject prior to about week 37 of pregnancy, contacting the sample with a reagent to a biomarker, to form a complex between the agent and the biomarker present in the sample; measuring the complex formed to determine the amount or concentration of said biomarker in the sample; wherein an increased likelihood of developing said disorder associated with pregnancy is indicated when said biomarker is at a level characteristic of a full term pregnancy.

The term "prognostic marker" or "biomarker" as used herein refers to a marker that informs about the outcome of a patient in the absence of systemic therapy or portends an outcome different from that of the patients without the marker, despite empiric (not targeted to the marker) systemic therapy.

The term "prognosis" as used herein, refers to the prediction of the likelihood a pregnancy associated disorder. In a specific example, the disorder is premature delivery.

The term "therapeutic monitoring" as used herein refers to the observation of the response of the subject to the treatment administered to it.

The determination, analysis or measurement of the biomarker is correlated with normal term pregnancy, or a disorder associated with pregnancy. In some examples, a patient sample is compared to a control sample. In some examples, a control is not used and qualitative or quantitative methods are used to determine the presence or absence, or amount or concentration of the protein of interest.

In one example, in determining whether there is strong, weak or minimal (or absent) amount of the biomarker, the patient sample may be compared to one or more control samples. In one example, a control sample has had known and/or established level of the biomarker. In one example, a control sample is a patient sample that has known and/or established levels of biomarker expression and/or known clinical outcome. In one example, a control is a cell line that has a known amount of biomarker expression. In another example, a control sample is a sample from a full term pregnancy.

The term "expression", as used herein, and for example in reference to a biomarker such as ccl2/CCL2, cxc1/CXCL1, cxcl10/CXCL10, a uterine activation protein (UAP), examples of UAPs include Fp and Otr, refers to all indicators of transcriptional expression of the biomarker encoding gene. In the foregoing it is understood that the first lower case term (e.g., "ccl2") refers to the mRNA and the upper case second term (e.g., "CCL2") refers to the protein. Such indicators include biomarker transcript products, generated as a result of transcription of the biomarker gene; translation products, including all forms of the biomarker protein, generated as a result of translation of the biomarker transcripts; and demonstrable or otherwise measurable biomarker activity.

As used herein, "biomarker protein", includes, but is not limited to, full-length proteins, mature proteins, pre-proteins, polypeptides, isoforms, mutations, variants, post-translationally modified proteins and variants thereof. Biomarker protein detection is know to the skilled worker, and is discussed herein.

Biomarker transcripts or mRNA can be measured using any of many techniques known to those of skill in the art, including, but not limited to, northern hybridization, PCR, reverse transcription followed by PCR, quantitative real-time PCR, nuclease protection assay, and in situ hybridization. Examples of biomarker mRNA includes, but is not limited to ccl2, cxc1, cxcl10.

Biomarker activity can be measured by a variety of assays known to those of skill in the art. A suitable method can be selected to determine the activity of proteins encoded by the biomarker genes according to the activity of each protein analyzed. For biomarker proteins, polypeptides, isoforms, mutations, and variants thereof known to have enzymatic activity, the activities can be determined in vitro using enzyme assays known in the art. Such assays include, without limitation, protease assays, kinase assays, phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

Biomarker protein can be measured/detected by a variety of techniques known to the skilled worker, including, but not limited to, immunoassays using a biomarker specific antibody. Protein levels can also be determined using a specific antibody or mass spectroscopy in conjunction with 2 dimensional gel electrophoresis (separation of proteins by their isoelectric point (IEF) in the first dimension followed by molecular weight determination using sodium dodecyl sulphate polyacrylamide gel electrophoresis (SDS-PAGE)).

In other examples, a biomarker protein is detected using a binding agent (also referred to an as agent) including, but not limited to, a lectin, nucleic acid (e.g. DNA, RNA), monoclonal antibody, polyclonal antibody, Fab, Fab', single chain antibody, synthetic antibody, aptamer (DNA/RNA), peptoid, zDNA, peptide nucleic acid (PNA), locked nucleic acid (LNA), synthetic or naturally occurring chemical compound (including but not limited to a drug or labeling reagent), dendrimer, or any combination thereof. In some instances, a single agent is used to detect a biomarker. In other instances, a combination of different agents is used to detect a biomarker Detection includes direct and indirect detection. Similarly, a binding agent can be directly or indirectly labeled.

The quantity of one or more biomarkers can be indicated as a value. The value can be one or more numerical values resulting from the evaluation of a sample, and can be derived, e.g., by measuring level(s) of the biomarker(s) in a sample by an assay performed in a laboratory, or from dataset obtained from a provider such as a laboratory, or from a dataset stored on a server.

In some examples, qualitatively or quantitatively determining, analyzing or measuring a biological sample from a subject for the presence or absence, or amount or concentration, of one or more prognostic marker associated, is carried out using antibodies to the biomarker.

In a specific example, antibodies of the present invention are immunoreactive or immunospecific for, and therefore specifically and selectively bind to a biomarker, for example the protein CCL2, CXCL1, CXCL10, a uterine activation protein (UAP), examples of UAPs include Fp and Otr. In one example, antibodies which are immunoreactive and immunospecific for the biomarker protein can be used. Antibodies for the biomarker protein are preferably immunospecific.

The term "antibody" and "antibodies" includes, but is not limited to, monoclonal and polyclonal antibodies. Antibodies may be derived from multiple species. For example, antibodies include rodent (such as mouse and rat), rabbit, sheep, camel, chicken, and human antibodies. In another example, antigen binding fragments which specifically bind to PDGFRα are used. In some example, the antibodies also comprise a label.

The term "label" as used herein is an identifiable substance that is detectable in an assay and that can be attached to a molecule creating a labeled molecule. The behavior of the labeled molecule can then be monitored and/or studied and/or detected.

Examples of labels include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate. The particular label used will depend upon the type of immunoassay. Antibodies can be tagged with such labels by known methods.

The term "binds specifically" refers to high avidity and/or high affinity binding of an antibody to a specific polypeptide e.g., an epitope of for the biomarker protein. Antibody binding to its epitope on this specific polypeptide is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at weak, yet detectable, level. Such weak binding, or background binding, is readily discernable from the specific antibody binding to the compound or polypeptide of interest, e.g., by use of appropriate controls, as would be known to the worker skilled in the art.

The methods of the present invention may be accomplished using any suitable method or system of immunohistochemistry. Non limiting examples include automated systems, quantitative IHC, semi-quantitative IHC, and manual methods.

The term "quantitative" immunohistochemistry refers to an automated method of scanning and scoring samples that have undergone immunohistochemistry, to identify and quantitate the presence of a specified biomarker, such as an antigen or other protein. For example, to quantitate for the biomarker protein, the score given to the sample is a numerical representation of the intensity of the immunohistochemical staining of the sample, and represents the amount of target biomarker present in the sample. As used herein, Optical Density (OD) is a numerical score that represents intensity of staining as well as the percentage of cells that are stained.

Automated sample processing, scanning and analysis systems suitable for use with immunohistochemistry are known in the art, and may be used with the methods described herein. Such systems may include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples.

Other examples that may be used in the detection, analysis or measurement of for the biomarker protein include, but are not limited to, immunoprecipitation, immunoblotting, mass spectrometry, quantitative fluorescence activated cell sorting, enzyme linked immunosorbent assay, immunohistochemistry, quantitative immunohistochemistry, fluorescence resonance energy transfer, Forster resonance energy transfer, and biomolecular fluorescence complementation.

It will be appreciated that in some circumstances, a patient which is initially identified a not having an increased likelihood of developing a pregnancy associated disorder, may relapse or reoccur. The methods as described herein may be used in the therapeutic monitoring of a patient, to monitor and identify those patients which may later develop a pregnancy associated disorder.

Methods of the present invention are conveniently practiced in the form of a kit.

In one example there is provided a kit for determining the likelihood of a pregnant subject undergoing term delivery, comprising: a reagent for determining a chemotactic activity of leukocytes from said pregnant subject; and instructions for the use thereof, wherein an increased likelihood of term delivery is indicated when said chemotactic activity of said leukocytes is at a level characteristic of a full term pregnancy.

In one example there is provided a kit for determining the likelihood of a pregnant subject undergoing preterm delivery, comprising: a reagent for determining a chemotactic activity of leukocytes from a pregnant subject prior to about week 37 of pregnancy; and instructions for this use thereof, wherein an increased likelihood of preterm delivery is indicated when said chemotactic activity of said leukocytes is at a level characteristic of a full term pregnancy.

In one example there is provided a kit for determining the likelihood of a pregnant subject developing a disorder associated with pregnancy, comprising: a reagent for determining a chemotactic activity of leukocytes from a pregnant subject prior to about week 37 of pregnancy; and instructions for the use thereof, wherein an increased likelihood of developing said disorder associated with pregnancy is indicated when said chemotactic activity of said leukocytes is at a level characteristic of a full term pregnancy.

In one example there is provided a kit for determining the likelihood of a pregnant subject undergoing term delivery, comprising: a reagent for measuring the amount or concentration of a biomarker in a sample a pregnant subject; and instructions for the use thereof, wherein an increased likelihood of term delivery is indicated when said biomarker is at a level characteristic of a full term pregnancy.

In one example there is provided a kit for determining the likelihood of a pregnant subject undergoing preterm delivery, comprising: a reagent for measuring the amount or concentration of a biomarker in a sample from a pregnant subject prior to about week 37 of pregnancy; and instructions for the use thereof, wherein an increased likelihood of preterm delivery is indicated when said biomarker is at a level characteristic of a full term pregnancy.

In one example there is provided a kit for determining the likelihood of a pregnant subject developing a disorder associated with pregnancy, comprising: a reagent for measuring the amount or concentration of a biomarker in a sample from a pregnant subject prior to about week 37 or pregnancy, wherein an increased likelihood of developing said disorder associated with pregnancy is indicated when said biomarker is at a level characteristic of a full term pregnancy.

In one non-limiting example, a kit comprises: a tube for centrifuging blood containing the appropriate amount of Polymorphoprep and marked with a 'fill' line for adding whole blood; PBS for resuspending the leukocytes; a two-chambered device separated by a microfilter with 5 micrometer pore size; a stand for holding the filter unit; PBS for the test chamber; and a chart with normal (healthy pregnancy) values for migrated leukocytes for each week (or month) of pregnancy.

To gain a better understanding of the invention described herein, the following examples are set forth. It should be understood that these examples are for illustrative purposes only. Therefore, they should not limit the scope of this invention in anyway.

EXAMPLES

Example I

Materials and Methods—I

This study was approved by the IRB of the Instituto Nacional de Perinatologia Isidro Espinosa de los Reyes in Mexico City (Register 212250-02181). Written, informed consent was obtained from each subject prior to inclusion in the study.

Tissues

Fetal membranes were collected aseptically from two groups: 1) Women with more than 37 weeks of gestation who developed spontaneous active vaginal delivery (TL) (n=5). Existence of labor was documented by cervical dilation ($\geq$4 cm) and contractility of the myometrium ($\geq$3 contractions of 40 s in 10 min by tocodynamometer) in the presence of spontaneous rupture of membranes (ROM). The duration of labor was similar between them (8-15 h). 2) Women with more than 37 weeks of gestation who underwent elective caesarean section and did not develop active labor (TNL) (n=5). Absence of cervical dilation, no uterine contractions, and integrity of the fetal membranes (absence of ROM) were documented. Women with premature rupture of membranes and those with microbiological or clinical evidence of cervicovaginal or intrauterine infection was present were excluded. Microbiological tests were performed in tissues by rolling a Dacron swab on the surface of the membranes. The swabs were cultured onto blood agar plates under aerobic and anaerobic conditions to ensure that tissues were free from infection. Women included in this study had internal monitoring and they were similar in ethnicity (Mexican Mestizo) and parity (primiparous). None of these women received antibiotics for prolonged ROM, oxytocin augmentation, or immunosuppressive or modulating medications.

Fetal Membrane Extracts

Immediately after delivery, the fetal membranes from both groups of women were sterile dissected from the placental edge and placed in a sterile phosphate-buffered saline solution (1×PBS). Within 30 min, membranes were washed thoroughly in sterile 1×PBS to remove blood and debris. From each fetal membrane we obtained fragments from the amnion, choriodecidua and whole fetal membranes randomly localized. We obtained 8-10 fragments of 6.5 cm-diameter using a sterile circular pattern and placed them in 75 $cm^2$ culture flasks. Immediately each explant was cultured (1 explant/1 flask) in 6.5 mL of Dulbecco-modified Eagle medium (DMEM), 1% MEM sodium pyruvate and 1% antibiotic-antimycotic [100 U penicillin, 100 µg streptomycin, 0.25 µg amphotericin B/Ml] for 24 h at 37° C. in a humid atmosphere containing 5% $CO_2$. Fetal calf serum-free conditions were used in all experiments. After this incubation, all explants were homogenized in their culture media using a Polytron (Brinkmann, USA) and pooled. Fetal membrane extracts were centrifuged at 14,000×g, the supernatant was filtered through a 0.2 µm membrane (Corning, USA), and preserved at −70° C. until use.

Leukocytes

Peripheral blood samples treated with heparin were collected from women fitting the same clinical characteristics as the groups described above (TL or TNL) n=(5 each). Polymorphonuclear and mononuclear leukocytes were isolated using a Ficoll gradient (Polymorphoprep, Axis-Shield, USA). Total leukocytes were then washed and cultured in RPMI medium supplemented with 10% fetal calf serum (FCS) and 1% antibiotic-antimicotic and cultured for 24 h at 37° C. in humidified air containing 5% $CO_2$. After incubation, leukocytes were extensively washed to eliminate FCS and suspended in the same FCS-free media as described above for the fetal membrane extracts. The number and viability of leukocytes were assessed by the trypan blue exclusion assay (>95%). All culture reagents were purchased from GIBCO Invitrogen Corporation.

Chemotaxis Assay

The chemotaxis assay was performed using a modified Boyden chamber (BY312; Neuro Probe, USA)[6,11]. Five hundred microliters of heterologous leukocyte suspension containing 500,000 leukocytes (1000 cells/$mm^2$ of filter area) were placed on top of the polycarbonate membrane (5 µm pore size; TMTP01300, Millipore Corporation, USA) with either fetal membrane extract (amnion, choriodecidua, or whole fetal membranes) or medium control as the chemoattractant in the lower compartment. Leukocytes were matched in the chemotaxis assays, thus extracts from TNL or TL women were tested with leukocytes from TNL or TL, respectively. Chambers were incubated for 90 min at 37° C. in humidified air containing 5% $CO_2$. Afterwards, chemoattracted cells were removed from the lower compartment and centrifuged at 500×g for 5 min at room temperature. The pellet was stained and analyzed by flow cytometry to identify the phenotype of chemoattracted heterologous leukocytes using conjugated monoclonal antibodies: total leukocytes/CD45-FITC (PN IM2643), T-lymphocytes/CD3-PC7 (6607100), B-lymphocytes/CD19-PC5 (PN IM2643), monocytes/CD14-ECD (PN IM2707U), and NK cells/CD56-PE (PN IM2073) (Beckman Coulter, USA). We considered granulocytes as $CD45^+CD3^-CD19^-CD14^-CD56^-$ cells. The flow cytometer (FC 500, Beckman Coulter) was set to analyze the samples for 300 s, which involved 10,000-100,000 events.

Statistical Analysis

The data were examined initially by the Shapiro-Wilk test for normal distribution and were found to not be normally distributed. Therefore the non-parametric Mann-Whitney test was used to differentiate statistical differences between groups (SPSS, version 16.0). Significance was achieved with $p \leq 0.05$.

Results—I

All fetal membrane extracts induced leukocyte chemotaxis. Whole fetal membrane extracts and separated choriodecidua extracts obtained from the TL group chemoattracted more leukocytes than those from the TNL group (n=5; p=0.01 and p=0.008 respectively). Extracts from the amnion, did not show differences between groups. Leukocyte chemotactic activity was greater in the choriodecidua extracts than in the amnion extracts obtained from TL tissues (n=5; p=0.016), however there was no difference between these two groups in the TNL extracts. In addition, whole fetal membranes had higher chemotactic activity than the amnion in TL tissues (n=5; p=0.029). The data also shows that the amnion and choriodecidua extracts obtained from TNL tissues chemoattracted the same number of leukocytes, and their activity did not show an additive effect when the fetal membranes were together (FIG. 1).

Figure 2:
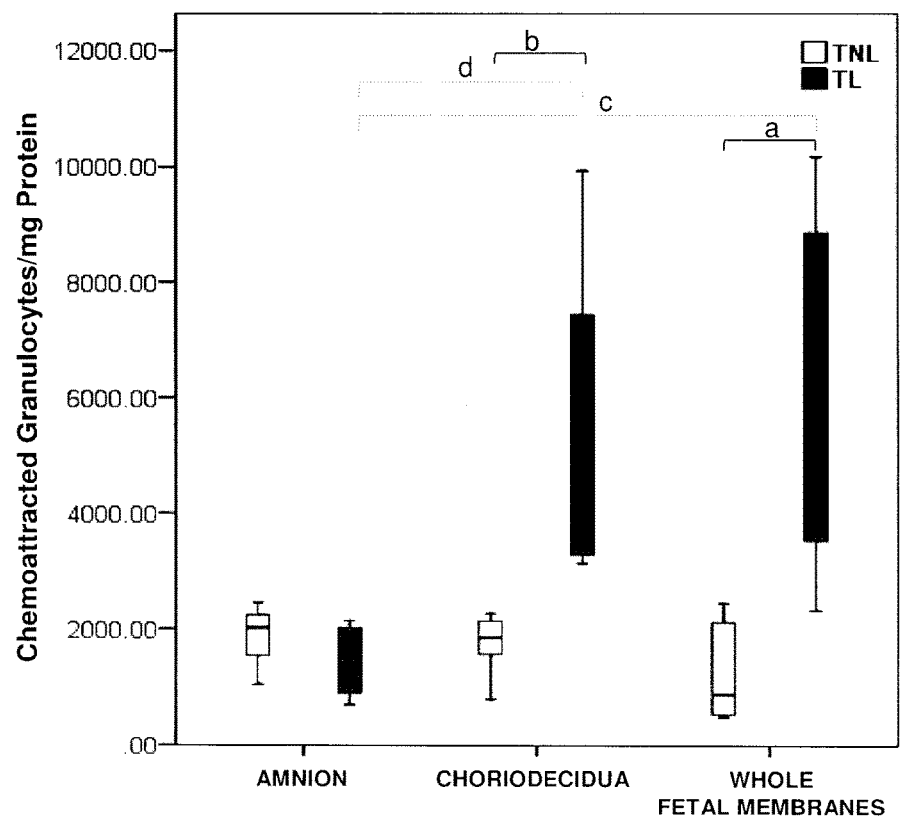
FIG. 2 is a graph depicting granulocyte chemotactic activity. The number of granulocytes chemoattracted by whole fetal membranes and the choriodecidua was significantly higher in TL compared with TNL (p=a0.019; b0.008). In TL tissues, the whole fetal membranes and choriodecidua extracts showed more leukocyte chemotactic activity than the amnion extracts (p=c0.029; d0.016). Data are presented as mean±SEM of chemoattracted leukocytes by each extract, from five different women per group, in triplicate.

Granulocytes were the main subset chemoattracted by all extracts. Granulocyte chemoattraction was higher in TL extracts than in TNL extracts both in the choriodecidua (p=0.008) and the whole fetal membrane extracts (p=0.019). In the amnion extracts, there was no significant difference in granulocyte chemoattraction between TL and TNL tissues. The choriodecidua (p=0.016) and the whole membrane (p=0.029) extracts from TL tissues chemoattracted more granulocytes than the amnion (FIG. 2).

Figure 3:
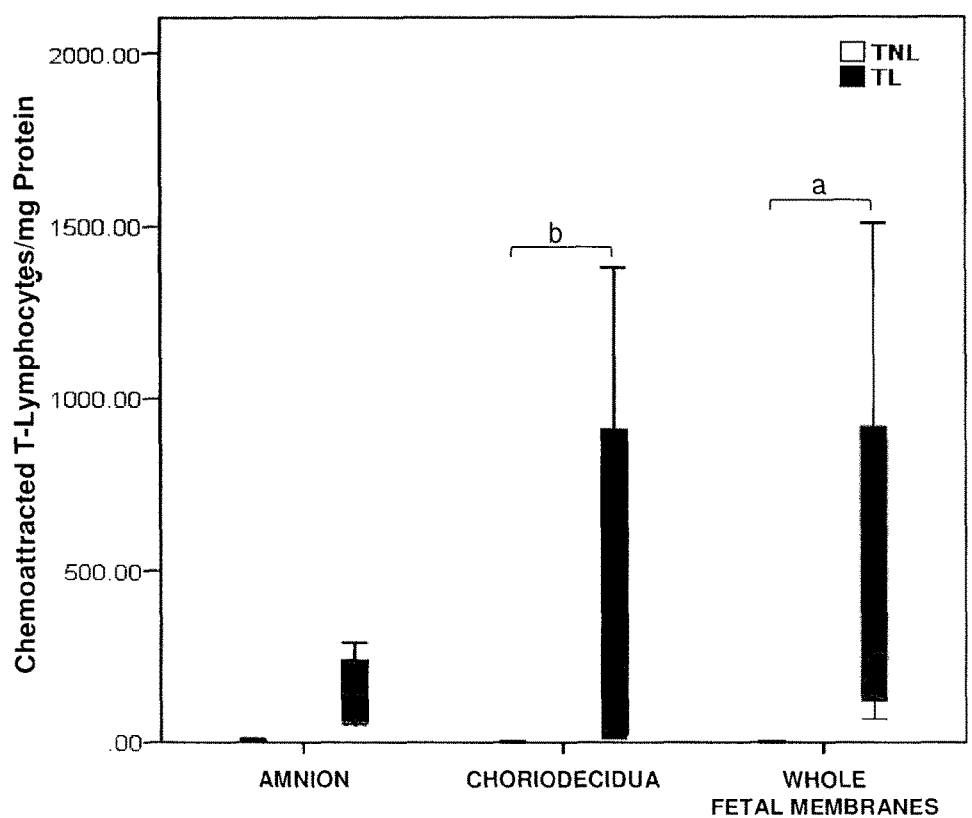
FIG. 3 is a graph depicting T-lymphocyte chemotactic activity. The number of T-lymphocytes chemoattracted by whole fetal membranes and the choriodecidua from TL was significantly higher than TNL (p=a0.010; b0.008). Data are presented as mean±SEM of chemoattracted leukocytes by each extract, from five different women per group in triplicate.

T-lymphocyte chemoattraction was greater in the choriodecidua (p=0.008) and the whole fetal membranes extracts (p=0.010) from TL compared with TNL (FIG. 3).

Figure 4:
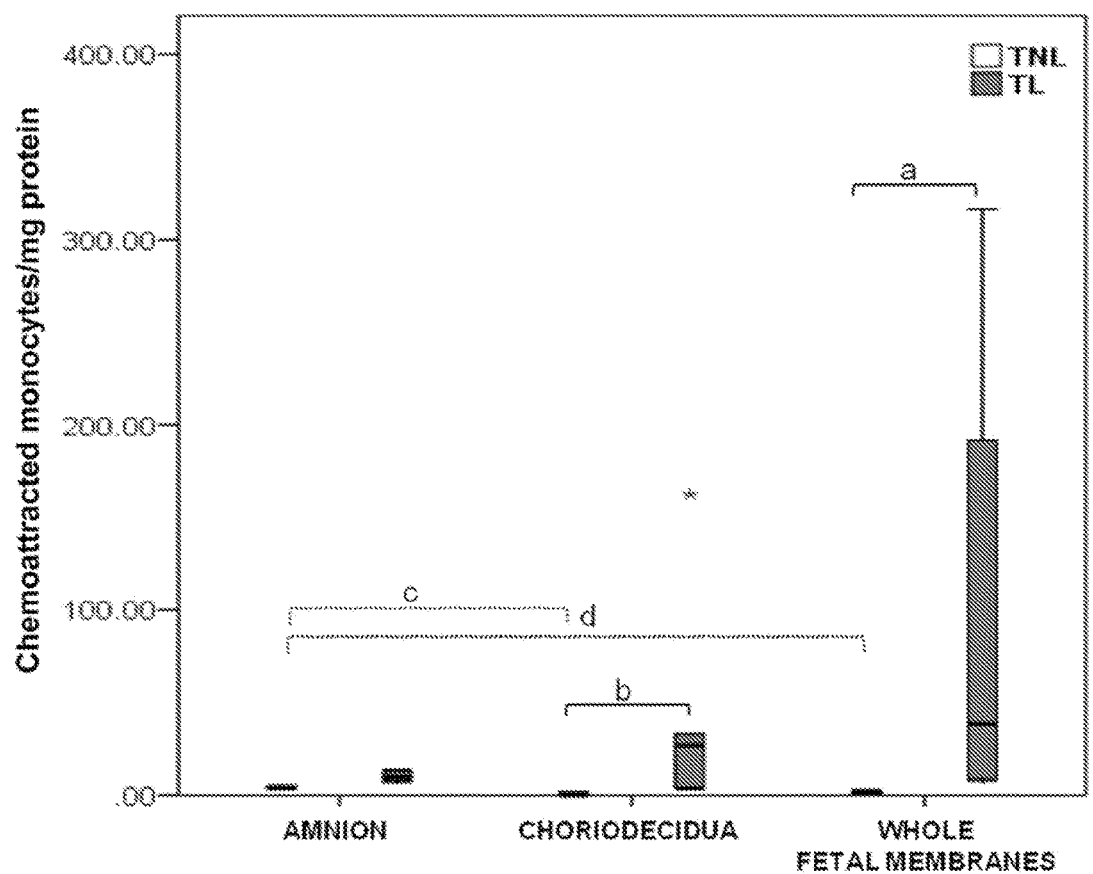
FIG. 4 is a graph depicting monocyte chemotactic activity. The whole fetal membranes and choriodecidua from TL chemoattracted significantly more monocytes than those from TNL (p=a0.010; b0.008). The amnion from TNL chemoattracted significantly more monocytes than the choriodecidua and whole fetal membranes from TNL (p=c0.036; d0.024). Data are presented as mean±SEM of chemoattracted leukocytes by each extract, from five different women per group, in triplicate.

Monocyte chemoattraction was also higher when whole fetal membrane (p=0.010) or choriodecidua extracts (p=0.008) from TL were compared with corresponding TNL extracts. In the TNL group, the amnion had higher monocyte chemotaxis than the choriodecidua (p=0.036) and the whole fetal membrane extracts (p=0.024) (FIG. 4).

Figure 5:
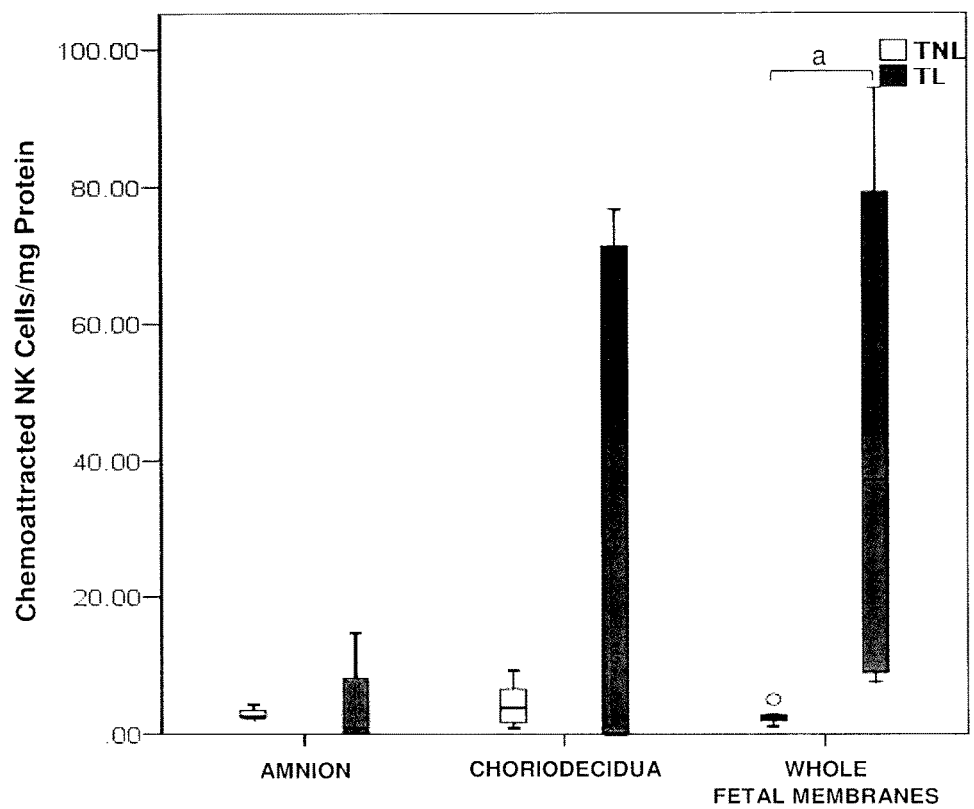
FIG. 5 is a graph depicting NK cell chemotactic activity. NK-cell chemoattraction was higher in the whole fetal membrane extracts from TL than TNL tissues (p=a0.010). There was no significant difference in NK cell chemoattraction between the amnion and the choriodecidua in TL and TNL. Data are presented as mean±SEM of chemoattracted leukocytes by each extract, from five different women per group, in triplicate.

NK cell chemoattraction was higher in the whole membrane extracts from the TL group compared to the TNL group (p=0.010). There were no significant differences in NK cell chemotaxis in TL and TNL amnion or choriodecidua extracts. However, it was observed that the choriodecidua had more NK-cell chemotactic activity than the amnion in TL tissues (FIG. 5).

Figure 6:
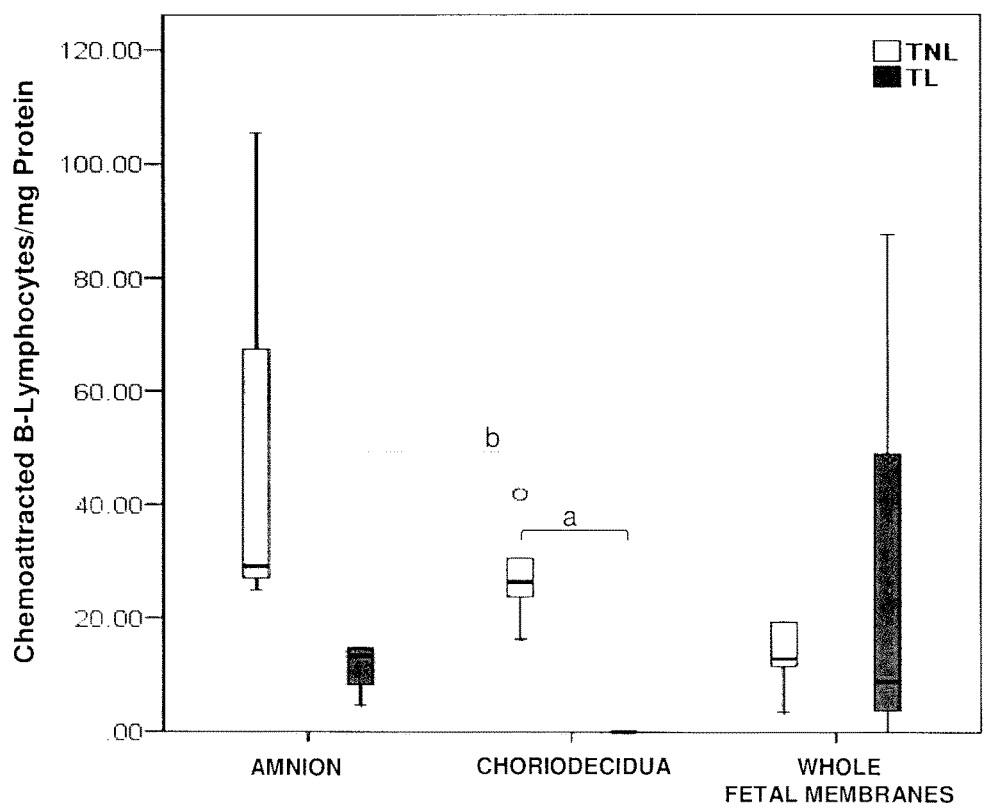
FIG. 6 is a graph depicting B-lymphocyte chemotactic activity. B-lymphocyte chemoattraction was significantly higher by choriodecidua with TNL than TL (p=a0.008). In TL, B-lymphocyte chemoattraction by the amnion was significantly higher than by the choriodecidua (p=b0.016). Data are presented as mean±SEM of chemoattracted leukocytes by each extract, from five different women per group, in triplicate.
Figure 8:
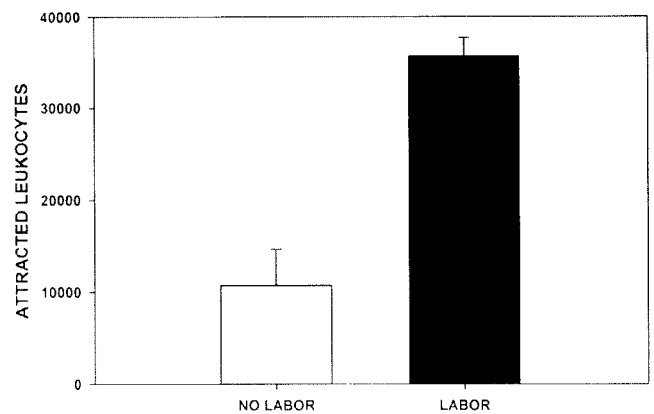
FIG. 8 is a graph depicting human fetal membranes (chorio-decidua) expressing chemotactic activity and this activity increases with labor at term. The increased chemotactic activity attracts more total leukocytes as assessed using the modified Boyden Chamber assay.
Figure 9:
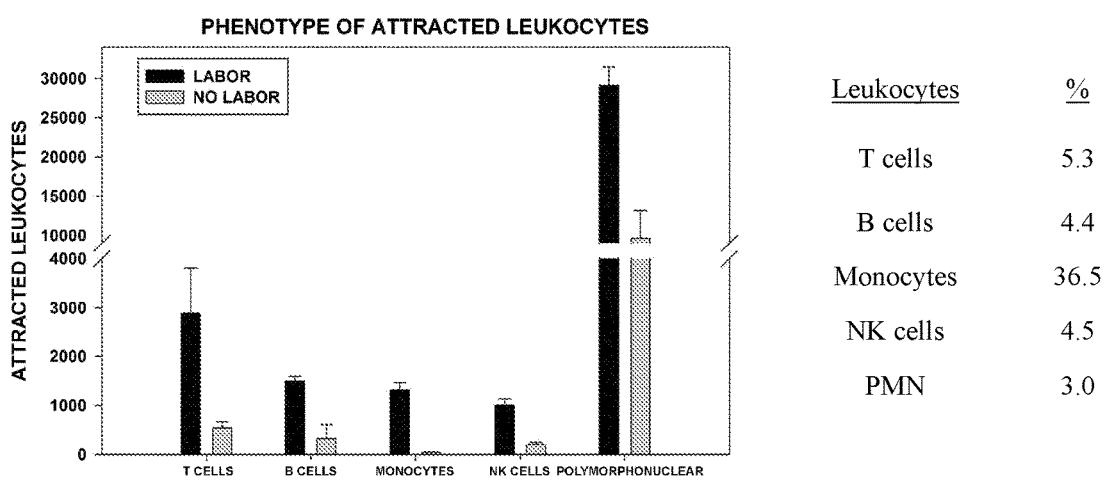
FIG. 9 is a graph depicting the increased chemotactic activity of the human chorio-decidua at term labor attracts selected populations of peripheral circulation leukocytes using the Boyden Chamber assay. The ratio of attracted leukocytes in labor compared to not in labor at term is demonstrated in the table.
Figure 10:
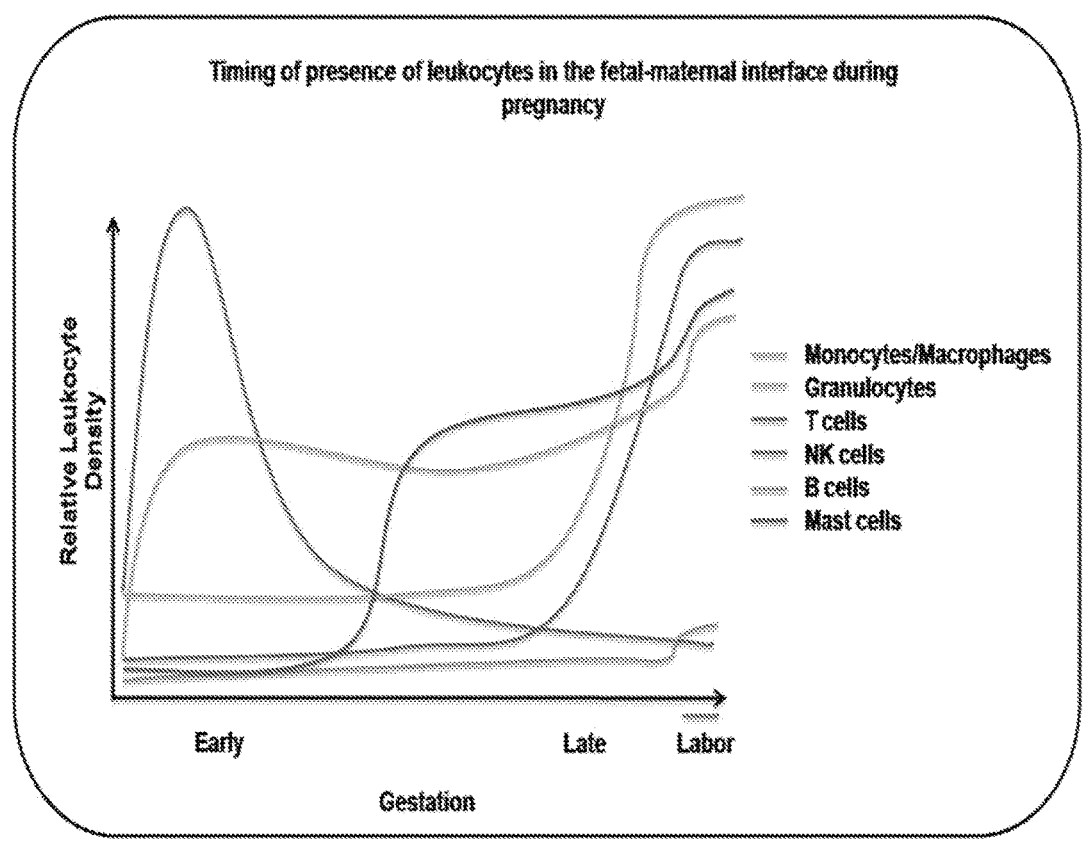
FIG. 10 is a graph depicting the timing of the infiltration of leukocytes into the human fetal-maternal interface (chorio-decidua) during pregnancy. This figure is based on our data and on literature values. It demonstrates the dynamic nature of leukocyte infiltration into the human uterus during pregnancy. Comparing peripheral leukocyte activation to established norms at any time during pregnancy can inform about pregnancy health.
Figure 12:
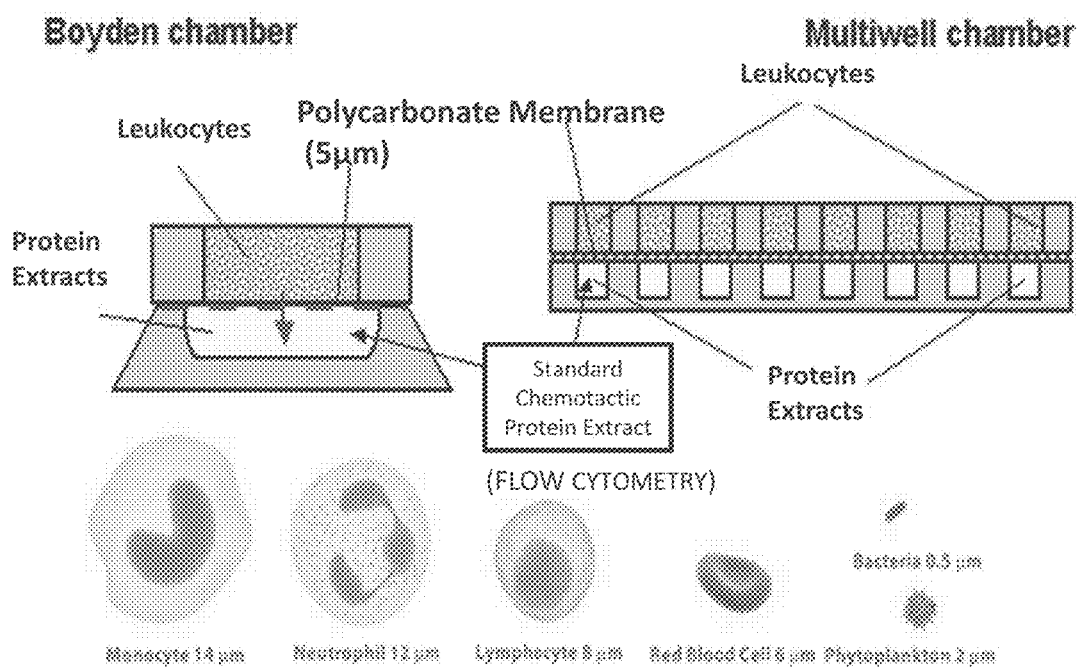
FIG. 12 a depiction of the chemotaxis assay. Isolated leukocytes are placed into the upper chamber and a standardized chemotactic protein extract from human chorio-decidua is placed into the lower chamber. The chemotactic protein extract 'attracts' leukocytes. Only activated leukocytes will migrate from the upper to the lower chamber as 'squeezing' through the small 5 µm pores is an active process. Size of representative leukocytes is shown along the bottom. The leukocytes are more receptive (or activated) to the chemotactic stimulus closer to impending labor, hence more of them will migrate to the lower chamber as the woman gets closer to delivery.
Figure 13:
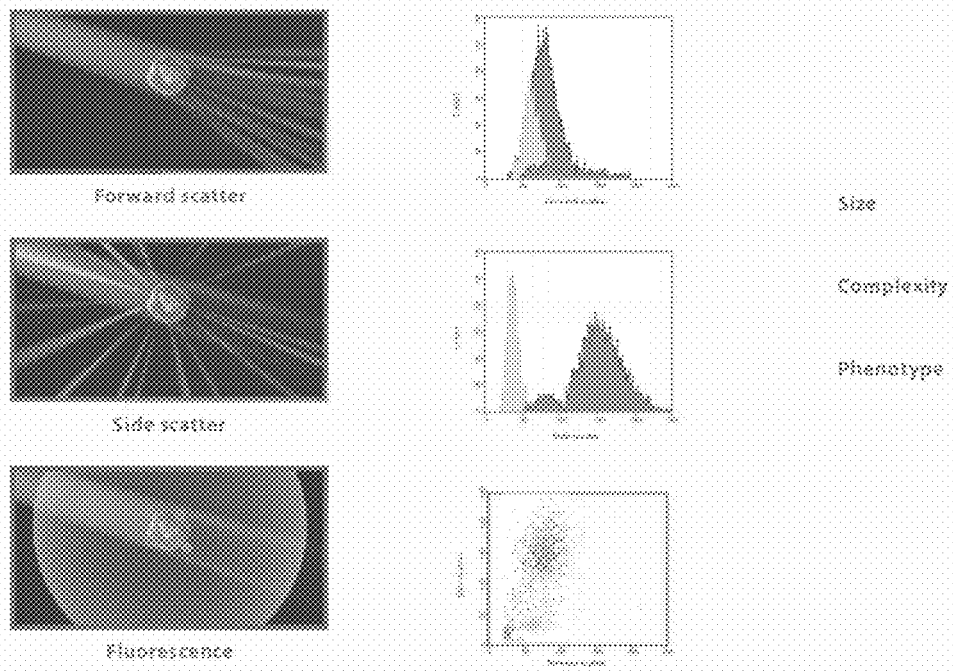
FIG. 13 depicts the number and type of leukocytes in the lower chamber are determined by flow cytometry which uses forward scatter, side scatter and fluorescence to specific cell surface protein markers to detect the type of leukocytes in the sample.
Figure 14:
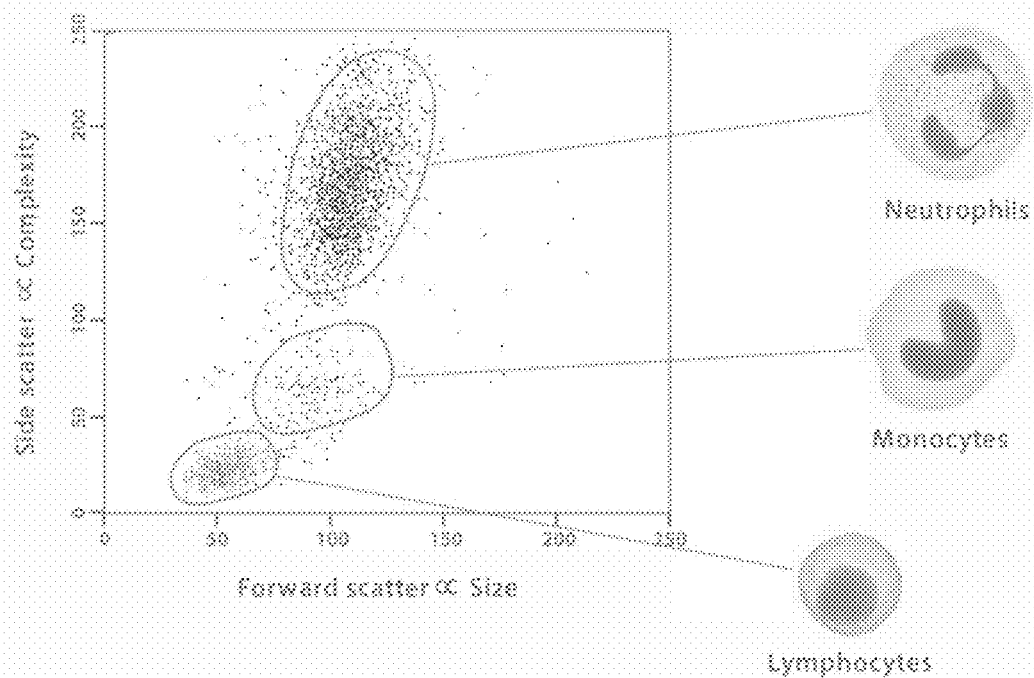
FIG. 14 depicts that forward and side scatter can be plotted to identify type of leukoctyes; density of individual events can be used to determine number of leukocytes in each category.

B-lymphocyte chemoattraction of the whole fetal membranes in TL and TNL was similar. However, the B-lymphocyte chemoattraction by the choriodecidua was significantly higher in TL than TNL extracts (p=0.008). The amnion chemoattracted a higher number of B-lymphocytes than the choriodecidua in TL extracts (p=0.016) (FIG. 6).

Discussion—I

The data herein demonstrate that during labor the amnion and the choriodecidua express differential leukocyte chemotactic activity, with this activity being higher in the choriodecidua.

The total leukocyte chemotactic activity of whole fetal membranes was not the result of an additive effect between the amnion and choriodecidua when tissues from women with labor were assayed.

It was also demonstrated that during labor, the choriodecidua extracts exhibit chemoattraction for granulocytes, T-lymphocytes, monocytes, and NK-cells. The amnion is responsible for B-lymphocyte chemoattraction.

It was also was shown that using tissues obtained before labor was present, the interaction between the amnion and choriodecidua is necessary for recruitment of monocytes.

There data indicate that once labor is present, the chemotactic activity of the fetal membranes may be mainly attributed to factors produced by the choriodecidua. Choriodecidua is a transitional tissue acting as an interface between the mother and the fetus. One of its functions throughout pregnancy is to act as a barrier to the maternal immune cells and this function is maintained during labor. In addition, during labor the choriodecidua chemoattracts specific subsets of leukocytes that are required for the conditioning of the proinflammatory milieu during labor and delivery. While not wishing to be bound by theory, this function was selectively expressed once labor was triggered or as a consequence thereof, since we did not find the same property in the choriodecidua extracts obtained from women in the absence of labor.

As demonstrated herein, there was a differential participation of the amnion and the choriodecidua in the recruitment of specific leukocytes subsets. While not wishing to be bound by theory, it is thought that this selective leukocyte recruitment is related to the specific roles of each leukocyte subset in labor.

The data herein showed that granulocytes were the most leukocyte subset chemoattracted by the fetal membranes and this chemoattraction is amplified in samples obtained in the presence of labor. In addition, most of the chemotactic activity is derived from the choriodecidua. The main subset of granulocytes is neutrophils, which are a rich source of inflammatory mediators in the body. They secrete pro-inflammatory cytokines, matrix metalloproteinases (MMPs), and extracellular matrix proteases, including neutrophil elastase and neutrophil collagenase[16-19]. Neutrophil-derived extracellular matrix proteases including MMP-8 and MMP-9 degrade extracellular matrix collagen, facilitating rupture of the fetal membranes[20]. Our studies indicate that leukocyte subsets in the fetal membranes at labor consist mainly of granulocytes and T-lymphocytes[14].

Again while not wishing to be bound by theory, eosinophils and basophils may also contribute to the population of granulocytes recruited to the fetal membranes at term. Possible roles for eosinophils in extracellular matrix remodeling of the fetal membranes and cervix have been suggested during late gestation[21].

T-lymphocytes were the second most abundantly chemoattracted leukocyte subset in the choriodecidua and whole fetal membranes at term. T-lymphocyte chemoattraction was increased in the choriodecidua and in the whole fetal membrane extracts in laboring tissues compared with the non-laboring tissues, indicating a role for T-lymphocytes in the induction of parturition. The specific role of T-lymphocytes in this process is unknown. As part of the adaptive immune system, T-lymphocytes play a role in the regulation of chronic inflammation, which suggests that the presence of T-lymphocytes in the fetal membranes during labor may occur as a result of previous maternal recognition of the fetus, and their actions may play a role in the regulation of this immunological response.

The data show that NK cell recruitment is higher in whole fetal membrane and choriodecidua extracts during labor; however this increase was only significant in whole fetal membrane extracts.

We did not observe an increase in B-lymphocyte chemoattraction into the whole fetal membranes before and during labor. However, during labor, this B-lymphocyte recruitment appeared to be mediated by the amnion, given that its extracts exhibited higher B-lymphocyte chemotactic activity than the choriodecidua extracts. The role of these cells in pregnancy is unknown and their concentration appears does not change during normal gestation[2]

Example—II

The timing of leukocyte activation in the maternal peripheral circulation relative to term delivery in the rat model was determined.

Methods—II

Maternal peripheral leukocytes were isolated by ficoll density gradient centrifugation from pregnant Long Evans rats at 17, 20 and 22 gestational days (GD) (n=5, delivery=22.5 GD). Simultaneously, cervix and uterus [upper, middle and lower segment] were obtained at 22 GD (n=5), and protein extracts containing chemotactic activity were isolated from them. The responsiveness (i.e. activity) of leukocytes from each time-point to the tissue protein chemotactic activity (LCA) was quantified using Boyden chambers and flow cytometry. As another measure of leukocyte activation, the Ccl2, Cxcl1 and Cxcl10 mRNA abundance was quantified by real time RT-PCR. Statistical analysis was performed by ANOVA and Games-Howell test.

Results—II

Peripheral LCA increased from 17 to 20 and 22 GD ($p=0.05$, each) in response to cervical chemotactic activity. In addition, leukocytes displayed consistent LCA increases to uterine (upper, middle and lower segments) chemotactic activity from 17 to 20 GD ($p<0.001$, each). Chemotactic activity from the upper uterine segment stimulated a further increase in LCA at GD 22 ($p<0.024$). In contrast, LCA reached a peak in response to chemotactic activity from the middle and lower uterine segment at GD 20, falling again on GD 22 ($p<0.0001$). Leukocyte Cxcl1 and Ccl2 mRNA abundance rose from 17 to 22 GD (7- and 3.3-fold), with a dramatic increase of Ccl2 mRNA abundance at 20 GD.

Discussion—II

Peripheral leukocyte activation increased consistently from 17 to 20 GD in response to chemotactic stimuli from cervical and uterine tissues with further increases at 22 GD to cervical and upper uterine activity. This activation includes increasing mRNA expression of Ccl2.

REFERENCES

1. KELLY R W. Inflammatory mediators and parturition. Rev Reprod 1996; 1:89-96.
2. THOMSON A J, TELFER J F, YOUNG A, et al. Leukocytes infiltrate the myometrium during human parturition: further evidence that labour is an inflammatory process. Hum Reprod 1999; 14:229-236.
3. OSMAN I, YOUNG A, LEDINGHAM M A, et al. Leukocyte density and pro-inflammatory cytokine expression in human fetal membranes, decidua, cervix and myometrium before and during labour at term. Mol Hum Reprod 2003; 9:41-5.
4. OSMAN I, YOUNG A, JORDAN F, GREER I A, NORMAN J E. Leukocyte density and proinflammatory mediator expression in regional human fetal membranes and decidua before and during labor at term. J Soc Gynecol Investig 2006; 13:97-103.
5. YOUNG A, THOMSON A J, LEDINGHAM M, JORDAN F, GREER I A, NORMAN J E. Immunolocalization of proinflammatory cytokines in myometrium, cervix, and fetal membranes during human parturition at term. Biol Reprod 2002; 66:445-9.
6. GOMEZ-LOPEZ N, ESTRADA-GUTIERREZ G, JIMENEZ-ZAMUDIO L, VEGA-SANCHEZ R, VADILLO-ORTEGA F. Fetal membranes exhibit selective leukocyte chemotaxic activity during human labor. J Reprod Immunol 2009; 80:122-31.
7. GOMEZ-LOPEZ N, GUILBERT L J, OLSON D M. Invasion of the leukocytes into the fetal-maternal interface during pregnancy. J Leukoc Biol 2010; In press.
8. SPRINGER T A. Traffic signals for lymphocyte recirculation and leukocyte emigration: the multistep paradigm. Cell 1994; 76:301-14.
9. ALBELDA S M, SMITH C W, WARD P A. Adhesion molecules and inflammatory injury. FASEB J 1994; 8:504-12.
10. GOMEZ-LOPEZ N, LARESGOITI-SERVITJE E, OLSON D M, ESTRADA-GUTIERREZ G, VADILLO-ORTEGA F. The Role of Chemokines in Term and Premature Rupture of the Fetal Membranes: A Review. Biol Reprod 2010; 82:809-814.
11. BOYDEN S. The chemotactic effect of mixtures of antibody and antigen on polymorphonuclear leucocytes. J Exp Med 1962; 115:453-66.
12. GOMEZ-LOPEZ N, ESTRADA-GUTIERREZ G, VADILLO-PEREZ L, VADILLO-ORTEGA F. Changes in leukocyte subpopulations in the choriodecidua and fetal membranes during human labor. Reprod Sci 2008; 15:86A.
13. GOMEZ-LOPEZ N, OLSON D M, CUBEIRO-ARREOLA K, VADILLO-ORTEGA F. T cell recruitment and contribution to an inflammatory microenvironment in the choriodecidua during human labor. Reprod Sci 2010; 17:69A.
14. GOMEZ-LOPEZ N, VADILLO-PEREZ L, OLSON D M, VADILLO-ORTEGA F. Differential leukocyte infiltration into peri-placental, middle and rupture zones of the human fetal membranes (FM) at term delivery: association with histology and physiology. Reprod Sci 2010; 17:69A.
15. MATSUBARA S, YAMADA T, MINAKAMI H, WATANABE T, TAKIZAWA T, SATO 1. Polymorphonuclear leukocytes in the fetal membranes are activated in patients with preterm delivery: ultrastructural and enzyme-histochemical evidence. Placenta 1999; 20:185-8.
16. BIRKEDAL-HANSEN H, MOORE W G, BODDEN M K, et al. Matrix metalloproteinases: a review. Crit Rev Oral Biol Med 1993; 4:197-250.
17. CASATELLA M N. The production of cytokines by polymorphonuclear neutrophils. Immunol Today 1995; 16:21-26.
18. HELMIG B R, ROMERO R, ESPINOZA J, et al. Neutrophil elastase and secretory leukocyte protease inhibitor in prelabor rupture of membranes, parturition and intra-amniotic infection. J Matern Fetal Neonatal Med 2002; 12:237-46.
19. OSMERS R, RATH W, ADELMANN-GRILL B C, et al. Origin of cervical collagenase during parturition. Am J Obstet Gynecol 1992; 166:1455-60.
20. MAYMON E, ROMERO R, PACORA P, et al. Human neutrophil collagenase (matrix metalloproteinase 8) in parturition, premature rupture of the membranes, and intrauterine infection. Am J Obstet Gynecol 2000; 183: 94-9.
21. TIMMONS B C, FAIRHURST A M, MAHENDROO M S. Temporal changes in myeloid cells in the cervix during pregnancy and parturition. J Immunol 2009; 182:2700-7.
22. VARGAS M L, SANTOS J L, RUIZ C, et al. Comparison of the proportions of leukocytes in early and term human decidua. Am J Reprod Immunol 1993; 29:135-40.
23. ABADIA-MOLINA A C, RUIZ C, MONTES M J, KING A, LOKE Y W, OLIVARES E G. Immune phenotype and cytotoxic activity of lymphocytes from human term decidua against trophoblast. J Reprod Immunol 1996; 31:109-23.
24. VEGA-SANCHEZ R, GOMEZ-LOPEZ N, FLORES-PLIEGO A, et al. Placental blood leukocytes are functional and phenotypically different than peripheral leukocytes during human labor. J Reprod Immunol 2010; 84:100-110.
25. TABIASCO J, RABOT M, AGUERRE-GIRR M, et al. Human decidual NK cells: unique phenotype and functional properties—a review. Placenta 2006; 27 Suppl A:S34-9.
26. BLIDARU I, ZUGUN F, CIANGA C, CARASEVICI E. [Maternal immunophenotypic profile in normal pregnancy and preterm birth]. Rev Med Chir Soc Med Nat Iasi 2002; 107:343-7.

Example III

In this example, maternal peripheral leukocyte activation in Long-Evans rats is shown.

Materials and Methods

Animals

Animal protocols were approved by the University of Alberta Health Sciences Animal Policy and Welfare Committee (#625/03/11/C), and the experiments were conducted in accordance with the Guidelines and Policies of Canadian Council on Animal Care (SOP.RES:RA:0001.0). Pregnant Long-Evans rats weighing 250-350 g were used in this study. Rats were housed in the University of Alberta Health Sciences Laboratory Animal Services.

Tissues and Blood

Rats were euthanized according to approved local policy with a lethal dose of Isoflurane (Halocarbon Products Corporation, USA) by inhalation in a large beaker at gestational days (GD) 17, 20 or 22. Parturition in this rat strain occurs at GD22.5. Blood by heart puncture (10 mL) and maternal-fetal tissues were collected in sterile conditions from postmortem rats. Maternal-fetal tissues included cervix, uterus, fetal membranes and placenta. The uterus was divided into three segments: upper (closest to the ovary), middle and lower (closest to the cervix). Tissues were washed in saline solution and placed immediately in RNALater (Ambion, Applied Biosystems, USA) or in liquid nitrogen (and then kept at −80° C.) until they were assayed.

Leukocytes and Serum

Blood samples were immediately divided into two tubes: 5 mL into a heparinized vacuum tube (BD Vacutainer, USA) and 5 mL into a 15 mL centrifuge tube (Corning Incorporated, USA). Serum was isolated from the centrifuge tube and stored at −20° C. until assayed. Polymorphonuclear and mononuclear leukocytes were isolated from the heparinized tube, using a Ficoll gradient (Polymorphoprep; Axis-Shield, Norton, USA), following the manufacturer's instructions. Total leukocytes were then washed in 1×PBS and the pellet was resuspended and stored in 500 μL of RNALater, or resuspended and incubated in supplemented RPMI medium 1640 (1% antibiotics [5,000 units of penicillin and 5,000 μg of streptomycin/mL] and 10% fetal bovine serum; Invitrogen, USA) at 37° C. for 24 h. Following the incubation time these leukocytes were used in chemotaxis assays.

Protein Extracts of Tissues

Tissues previously placed in liquid nitrogen were gradually defrosted. Tissues were cut in fragments of ~1 cm³ and homogenized in 1 mL of DMEM (High Glucose 1× and 1% antibiotics; Invitrogen, USA) using a Polytron (Polytron PRO200 homogenizer, PRO Scientific, USA). These extracts were centrifuged at 4° C., 12,000×g for 30 min, repeating this last step until a clear supernatant was obtained. Protein extracts then were stored at −20° C. until use.

Chemotaxis Assay

The chemotaxis assay was performed using a modified validated Boyden chamber assay (AP48; Neuro Probe, USA) (Boyden, 1962; Chen, 2005; Gomez-Lopez et al., 2009, 2011). Fifty μL of leukocyte suspension containing 100,000 leukocytes were placed on top of the polycarbonate membrane (5 μm pore size; PFB5, Neuro Probe, USA) with either protein extracts of tissues or medium control as chemoattractant in the lower compartment. Heterologous leukocytes were matched in chemotaxis assays; protein extracts of tissues at GD17, 20 and 22 were tested with leukocytes at GD22, and leukocytes at GD17, 20 and 22 were tested with protein extracts (uterus and cervix) at GD22. Chambers were incubated for 120 min at 37° C. in humidified air containing 5% $CO_2$. Incubation time was previously established by performing incubation time curves (Gomez-Lopez, 2011). Afterwards, chemoattracted leukocytes were removed from the lower compartment and centrifuged at 500×g for 5 min at room temperature. The pellet was fixed with 500 μL of OptiLyse® B Lysing Solution (Beckman Coulter, USA) and counted by flow cytometry. The flow cytometer (FACSCANTO II, http://flowcytometry.ualberta.ca/) was set to analyze the samples for 30 s, which involved 10,000-100,000 events. The coefficient of variance of this method (inter and intra assay) is <5%.

Flow Cytometry

Blood taken by heart puncture was labelled with the following fluorochrome-conjugated anti-rat mAb: CD45-Alexa Fluor 488 for total leukocytes (clone OX-1, #202205; BioLegend, USA), OX43-PE for monocytes/macrophages (sc-53109; Santa Cruz Biotechnology, USA), CD45R-PE for B cells (clone HIS24; #554881; BD Pharmingen, USA), CD161-Alexa Fluor 647 for NK cells (10/78; #203110; BioLegend) and CD3-FITC/CD4-PC7/CD8-APC for T cells (clones 1F4, OX-38, OX-8; # PN A32909; Beckman Coulter, USA). Additionally, we identified mast cells using a primary purified mouse anti-rat Mast cells (clone: AR32AA4; #551770; BD Pharmigen) and a secondary rabbit anti-mouse $IgG_{2a}$-PE (sc-3765; Santa Cruz Biotechnology). Granulocytes were identified as $CD45^+OX43^-CD45R^-CD161^-CD3^-$. Leukocytes were then fixed using 500 μL of OptiLyse B (Beckman Coulter), washed, and resuspended in 500 μL of 1×PBS to be analyzed by flow cytometry. Phenotype of leukocytes was analyzed within the $CD45^+$ and $CD3^+$ region, respectively.

RNA Extraction, cDNA Synthesis and RT-PCR Real Time

RNAlater was removed from the tissue samples and leukocytes by aspiration or centrifugation, respectively. Total RNA was isolated from them using Trizol (Invitrogen, USA) following the manufacturer's instructions. Total RNA concentration was quantified using the spectrophotometer ND-1000 (Thermo Fisher Scientific Inc, USA). Total RNA concentration was determined with spectrophotometer at 260 nm optical density. The RNA purity was assessed by the optical density ratio 260 nm/280 nm (~2.0). cDNA was synthesized from 500 ng of total RNA using the gScript™ cDNA SuperMix (Quanta BioSciences, USA), following manufacturer's instructions. Real time PCR (RT-PCR) was performed using the SYBR Green FastMix (Quanta BioScience, USA) and the iCycler apparatus (Bio-Rad, USA). Primers for rat chemokines and UAPs were designed using the Primer Premier 5 software (Table 1, see FIG. 21). The cDNA obtained was then used in subsequent PCR reactions.

Each reaction contained 1 μL of cDNA (50 ng/μL), 10 μL of SYBR green FastMix, 0.5 μL of forward primer (10 μM), 0.5 μL of reverse primer (10 μM) and sterile water in a total reaction volume of 20 μL. Real time RT-PCR was performed under the following conditions: 10 min at 95° C., followed by 40 cycles of 15 s at 95° C. and 1 min at 60-62° C. (Table 1, see FIG. 21). To control for amplification of non-specific products, melt curve analysis was performed following amplification by measuring fluorescence while increasing temperature in 0.5° C. increments from 55° C. to 95° C. No amplification of non-specific products was observed with each set of primers. Standard curves for each gene were generated by serial dilutions of pooled cDNA samples. The amplification efficiency for each primer set was determined by converting the slope of the standard curve using the algorithm $E=10^{-1/slope}$. For each gene, the mean threshold cycle (from duplicate reactions) was corrected for the efficiency of the reaction and expressed relative to a control sample for each experiment. Rat chemokine and UAP levels were then expressed relative to Cyp levels (Pfaffl, 2001).

ELISAs

ELISAs for rat CXCL1 (#RCN100; R&D Systems, USA), CXCL10 (#E90371Ra; USCN Life Science, CN) and CCL2 (#KRC1011, Invitrogen, USA) were performed in protein extracts of tissues following manufacturer's instructions. ELISAs for P4 (#PG129S-100, Calbiotech, USA) and E2 (#ES180S-100, Calbiotech) were performed in both serum and protein extracts of tissues following the manufacturer's instructions. The protein concentration of protein extracts were measured with Protein Assay Reagent (Precision Red™, Cytoskelton, USA) at UV-vis 600 nm by the ND-1000. Chemokine and hormonal concentrations were normalized with protein concentrations.

Statistical Analyses

The data were examined initially by the Shapiro-Wilk test for normal distribution. When data were normally distributed, analysis of variance was performed where variation was proportioned to gestational days. When a significant F value was obtained, post hoc testing identified differences between gestational days. The Kruskal-Wallis and Mann-Whitney U tests were used when the data were not normally distributed. Statistical analyses were performed using SPSS (SPSS Inc, USA), version 18.0. A P value of ≤0.05 was considered statistically significant.

Results—III

Leukocyte Migration—Chemotactic Responsiveness

Figure 15:
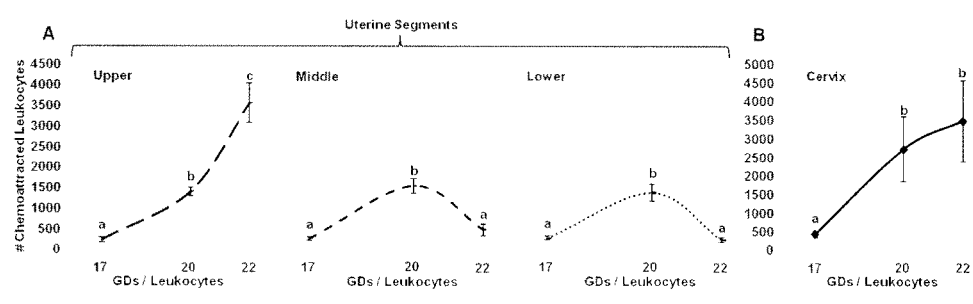
FIG. 15. Leukocyte responsiveness to uterine and cervical chemotactic signals. Total peripheral leukocytes from GD17, 20 and 22 were tested in chemotaxis assays using extracts from different uterine segments (A) and cervix (B) obtained on GD22. Leukocyte responsiveness on GD20 was higher than on GD17 in all cases, and it also was higher on GD22 than on 20 only in response to upper uterine segment and cervical extracts. Data are presented as mean±SEM of attracted leukocytes in triplicate by each group of tissues (n=5 each). Means with different letters are significantly different.

First, we investigated the onset of peripheral leukocyte migration or chemotaxis during gestation in response to uterine and cervical extracts obtained at term. Chemotaxis assays were performed using extracts from cervical and uterine tissues obtained on GD22 and maternal peripheral leukocytes obtained on GD17, 20 and 22. The data show that there is a uniform increase in leukocyte migration on GD20 compared to GD17 in response to term chemotactic signals from all three uterine segments and the cervix (p<0.05, FIG. 15). This high leukocyte responsiveness was increased further at GD22 (p=0.024) in response to chemotactic factors extracted from the upper uterus (FIG. 15A), maintained at a high level in GD22 leukocytes responding to chemotactic cervical extracts, and returned to GD17 levels when GD22 leukocytes were tested against GD22 middle and lower uterine segment extracts (FIG. 15B, C. These data identify peripheral leukocyte activation or chemotaxis as among the earliest known events associated with the birth cascade. They also suggest that different chemotactic signals emanate from the different uterine regions and cervix and that the population of peripheral leukocytes is changing either in numbers of cells or their responsiveness to chemotactic signals (or both).

Leukocyte Activation—Expression of Chemokines

In addition to demonstrating the early activation of peripheral leukocytes in terms of chemotaxis, we ascertained whether there are other signs of early activation of leukocytes. We next studied the expression of chemokines by peripheral leukocytes (FIG. 16). It is evident that ccl2 expression in peripheral leukocytes is increased significantly (p<0.02, Kruskall-Wallis, FIG. 2A) between GD17 and 20 and maintained until GD22, but that neither cxcl1 nor cxcl10 significantly changed (FIG. 16B, C (not significant), and indeed it appears that mean levels of cxcl10 decrease.

We also determined the mRNA expression of FP and OTR in leukocytes from these gestational ages; there were no significant differences (data not shown).

Leukocyte Subsets—Maternal Peripheral Circulation

Figure 17:
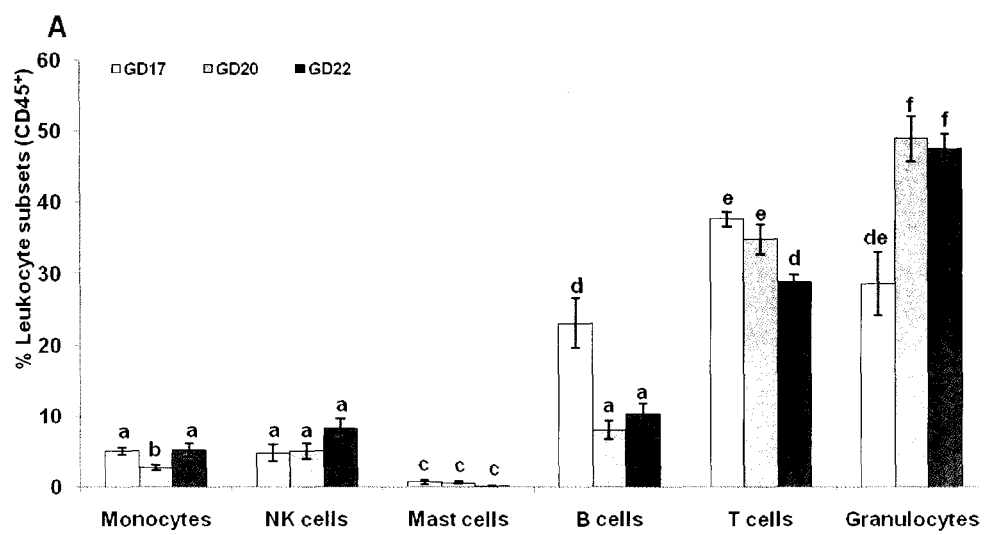
FIG. 17. Leukocyte subsets in the maternal periphery. A. Total Leukocytes. Monocyte proportions decreased from GD17 to 20 and increased from GD20 to 22. T cells decreased and granulocytes increased on GD22 in comparison to GD20. Data are presented as mean±SEM of determinations in duplicate per group of tissues (n=5 each). Means with different letters are significantly different.

Given that we demonstrated an early responsiveness between GD17 and 20 of peripheral leukocyte migration to term uterine chemotactic factor, and that peripheral leukocytes increase their expression of ccl2 at this time, the possibility exists that individual leukocyte populations could be changing in the maternal peripheral circulation in late gestation. Such changes could be early events in the birth cascade for labour. Some significant changes in the proportions of leukocyte subsets in the maternal periphery were found (FIG. 17). Monocytes decreased from GD17 to 20 (p=0.008) but then increased to GD22 (p=0.032). B cells decreased from GD17 to 20 (p=0.016), and their proportions remained stable. Between GD 20 and 22 T cells decreased (p=0.032 and 0.016, relative to GD20 and 17, respectively), but granulocytes increased (p=0.016 and 0.032, FIG. 17A).

Maternal Fetal Tissue Activation—Expression of Chemotactic Factors

Figure 18:
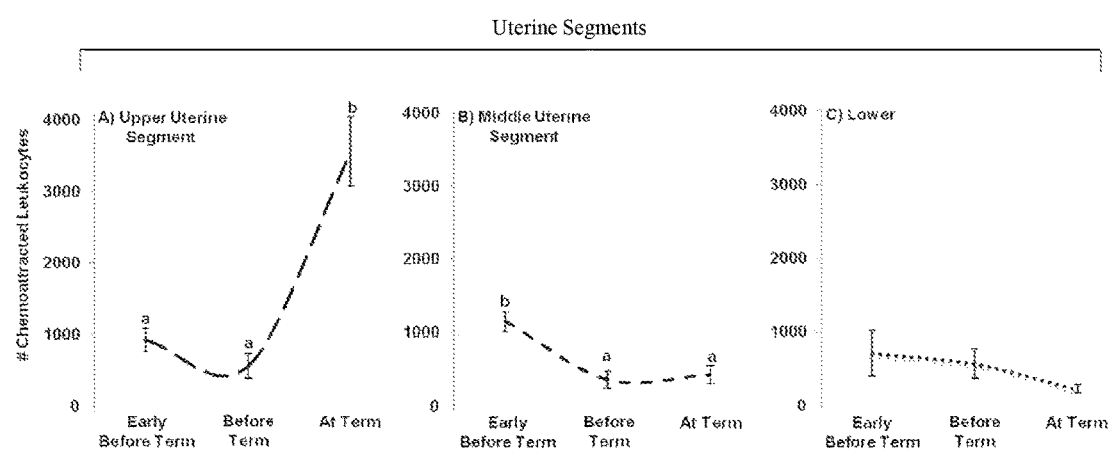
FIG. 18. Leukocyte chemotaxis of maternal and fetal tissues. Maternal and fetal tissues from GD17, 20 and 22 were tested in chemotaxis assays using leukocytes on GD22. Uterine segments (upper; middle; lower). Upper uterine segment extracts have higher leukocyte chemotaxis on GD22 than on 20; in contrast, middle uterine segment extracts have lower leukocyte chemotaxis on GD22 than on 20. Data are presented as mean±SEM of attracted leukocytes in triplicate by each group of tissues (n=5 each). Means with different letters are significantly different.
Figure 19:
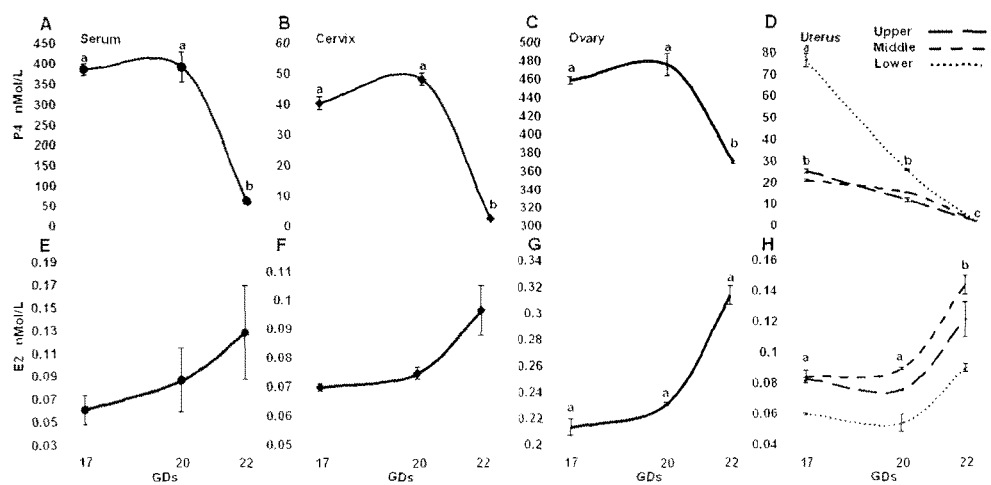
FIG. 19. Progesterone (P4) and estradiol-17β (E2) concentrations in serum and reproductive tissues. P4 (A, B, C, D) and E2 (E, F, G, H) concentrations are shown on the y-axis, and each GD is represented on the x-axis. A and E in serum, B and F in cervix, C and G in ovary, D and H in uterus. Data shown are means±SEM of determinations in duplicate per group (n=5 each). Means with different letters are significantly different. P4 decreased and E2 increased in all cases from GD20 to 22.
Figure 20:
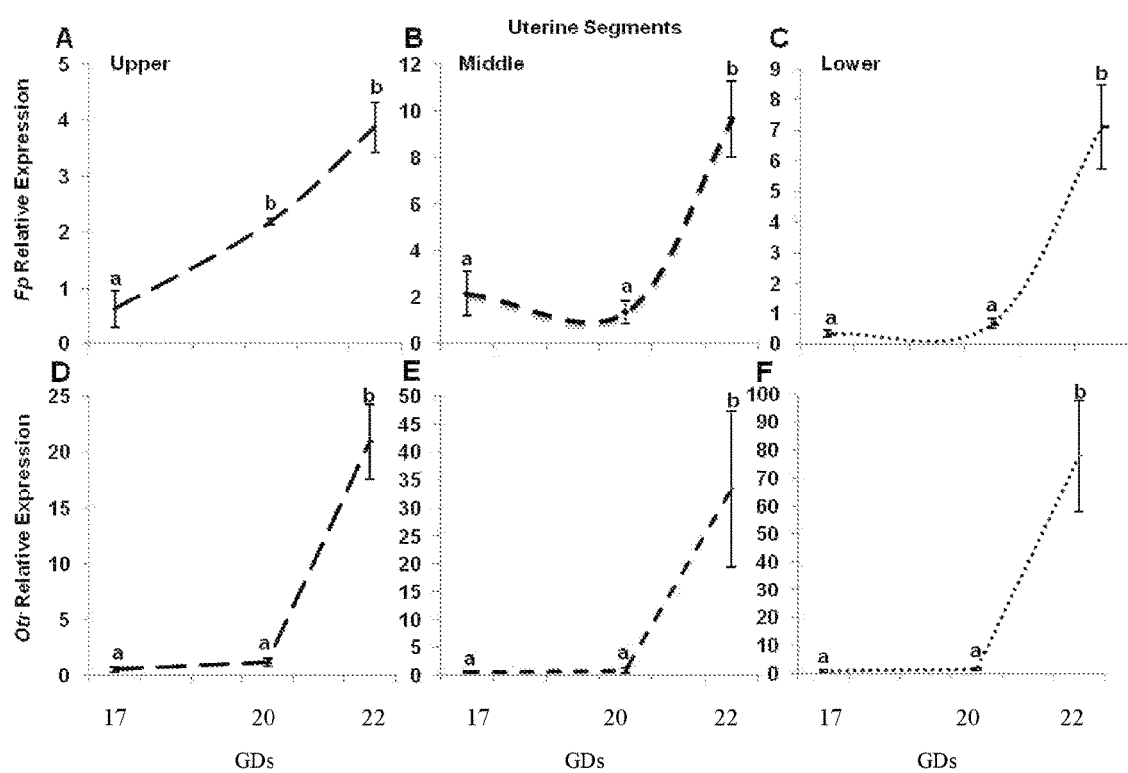
FIG. 20. Relative expression of UAPs in uterine segments. Relative expression of Fp (A, B and C), and Otr (D, E and F) is shown on the y-axis, and each GD is represented on the x-axis. Fp and Otr levels were higher on GD22 than on 17 and 20 in all of the cases (p<0.05). Data shown are means±SEM of determinations in duplicate per group (n=5 each). Means with different letters are significantly different.

We investigated the time-course of chemotactic factor expression by the maternal-fetal tissues during late gestation. Chemotactic activity assays were performed using chemotactic factors extracted from maternal-fetal tissues from GDs 17, 20 and 22 in late pregnancy and leukocytes obtained on GD22. The upper uterine segment showed higher leukocyte chemotactic activity on GD22 than on 20 and 17 (p=0.005 and 0.009, FIG. 18), and this increase was higher than in other segments (p<0.05, ~4 fold increase, FIG. 19). On GD 17, the middle uterine segment had slightly higher leukocyte chemotactic activity than on GD20 and 22 (p=0.002 each, FIG. 18). In the lower uterine segment there were no significant differences in the leukocyte chemotactic activity (FIG. 18). The cervix had the highest overall chemotactic activity (p<0.05, which reached a peak on GD 20, but this was not greater than earlier or later in gestation in cervix, and the fetal membranes and placenta had the lowest chemotactic activities of all tissues and showed no changes in late gestation (data not shown).

P4 and E2 Concentrations in Serum and Tissues

We observed the classical shift in the steroid hormone concentrations as evidenced by a P4 fall and E2 rise, which occurred between GD 20 and 22 in peripheral serum, cervix and all uterine regions for P4 (p≤0.014; FIG. 19A-C); whereas E2 levels tended to increase from GD20 to 22, but this increase was significant only in uterus (p<0.039) (FIG. 23D-G).

Maternal Uterine Activation—UAP Expression

We correlated these immunological and steroid hormone changes with the expression of two key UAPs, Fp and Otr, which are ultimately responsible for preparing the uterus for labour and delivery. In the upper uterine segment, Fp levels increased early and significantly between GD 17 and 20 (p=0.045, FIG. 21A), and they continued to increase to GD22 although they were not significantly different. In both middle and lower segments, its levels increased later, between GD20 and 22 (p=0.013 and 0.006 each for GD 20 and 17, respectively, FIG. 21 B,C). Uterine Otr levels increased consistently in each uterine segment from GD20 to 22 (p=0.027, 0.001, and 0.0001, respectively; FIG. 21D-F).

Discussion—III

The data of this study demonstrate that the maternal peripheral leukocytes display some of the earliest changes (by GD20) that precede parturition in the Long-Evans rat. The most telling of these is their ability to increase their migration through a Boyden chamber in response to a term uterine or cervical chemotactic stimulus. Next is the ability to increase their expression of ccl2, and early changes in the relative proportions of monocytes, B cells and granulocytes. Later, between GD 20 and 22, further changes occur in leukocytes, serum, uterus, cervix, fetal membranes and placenta (some data now shown). These include increased activity of chemotactic factors and expression of specific chemokines, changes in tissue and circulating levels of steroids, and the up-regulation of UAPs. These data indicate that the activation of maternal peripheral leukocytes is an early step in the birth cascade. Subsequent steps could include the invasion of uterine tissues by activated leukocytes where they contribute to creating local inflammatory microenvironments that promote parturition through stimulation of chemokines and chemokine activity and the stimulation of UAP expression.

The Long-Evans rat is an appropriate model for studying the relationships between peripheral leukocyte activation, chemokine activity, and uterine activation. (Denucci et al., 2010; Faraji et al., 2011; Paris et al. 2010). Unlike the Sprague-Dawley rat [BF Mitchell et al.; E Hirsch et al.], the Long-Evans rat is sensitive to administration of interleukin (IL)-1β on GD17 in that it delivers 36 h early and specific antagonism of the IL-1 receptor I delays term delivery by 17 h (unpublished data). Another advantage over the Sprague-Dawley rat model is that the Long-Evans dam is 50% or more larger thereby facilitating collection of blood and tissues.

The Boyden chamber migration assay is a very sensitive technique for assessing leukocyte responsiveness to chemotactic signals. To our knowledge, this is the first time it has been used in an animal study with the purpose of delineating temporal events in the birth cascade. Here we used term chemotactic activity extracted from various tissues and tested it against leukocytes collected at different times in late gestation to demonstrate the changing attractiveness of leukocytes to the same chemotactic signals as gestation progressed.

The upper uterine segment and the cervix are interesting not only in their respective roles in parturition (contraction vs. softening and effacement), but each produced term chemotactic activity that attracted more leukocytes on GD20 than GD17. Further, the upper uterine segment saw a significant increase in FP mRNA expression on GD20. These changes in upper uterus and cervix did not correlate well, however, with mRNA or protein expression of three key chemokines, CCL2, CLCL1, or CXCL10 in these same tissues. Hence in upper uterus and cervix, either the composition of the chemotactic extracts is unique to each tissue or uterine segment and to changing gestation and/or the responsiveness of peripheral leukocytes to these factors is dynamic and changes rapidly in late gestation.

The data show that the uterine segments have differential leukocyte chemotaxis. We demonstrated that at term of pregnancy, the upper uterine segment has high leukocyte infiltration.

In conclusion we demonstrated that the maternal peripheral leukocyte activation as defined by migration to term chemotactic stimuli, expression of ccl2, and changes in relative proportions in peripheral blood, precedes uterine tissue chemotactic activity expression, or the changes in steroid hormone concentrations and UAPs typical of the termination of pregnancy.

REFERENCES

Abbas A K, Lichtman A H & Pillai S. (2010). *Cellular and molecular immunology*, vol. 280. Saunders Elsevier, Philadelphia, Pa., USA.

Arthur P, Taggart M J, Zielnik B, Wong S & Mitchell B F. (2008). Relationship between gene expression and function of uterotonic systems in the rat during gestation, uterine activation and both term and preterm labour. *The Journal of Physiology* 586, 6063-6076.

Bazer F W, Spencer T E, Johnson G A, Burghardt R C & Wu G. (2009). Comparative aspects of implantation. *Reproduction* 138, 195-209.

Bokstrom H, Brannstrom M, Alexandersson M & Norstrom A. (1997). Leukocyte subpopulations in the human uterine cervical stroma at early and term pregnancy. *Hum Reprod* 12, 586-590.

Bowen J M, Chamley L, Keelan J A & Mitchell M D. (2002). Cytokines of the placenta and extra-placental membranes: roles and regulation during human pregnancy and parturition. *Placenta* 23, 257-273.

Boyden S. (1962). The chemotactic effect of mixtures of antibody and antigen on polymorphonuclear leukocytes. *J Exp Med* 115, 453-466.

Bukovsky A & Presl J. (1979). Ovarian function and the immune system. *Med Hypotheses* 5, 415-436.

Bulmer J N, Morrison L, Longfellow M, Ritson A & Pace D. (1991). Granulated lymphocytes in human endometrium: histochemical and immunohistochemical studies. *Hum Reprod* 6, 791-798.

Butcher E C. (1991). Leukocyte-endothelial cell recognition: three (or more) steps to specificity and diversity. *Cell* 67, 1033-1036.

Challis J R G, Matthews S G, Gibb W & Lye S J. (2000). Endocrine and paracrine regulation of birth at term and preterm. *Endocrine reviews* 21, 514-550.

Chen H C. (2005). Boyden chamber assay. *Methods Mol Biol* 294, 15-22.

Chwalisz K, Benson M, Scholz P, Daum J, Beier H M & Hegele-Hartung C. (1994). Cervical ripening with the cytokines interleukin 8, interleukin 1 beta and tumour necrosis factor alpha in guinea-pigs. *Hum Reprod* 9, 2173-2181.

Cook J L & Olson D M. (1999). The role of uterine prostaglandins in the initiation and maintenace of labour. *Fetal and Maternal Medicine Review* 11, 69-78.

Denucci S M, Tong M, Longato L, Lawton M, Setshedi M, Carlson R I, Wands J R & de la Monte S M. (2010). Rat strain differences in susceptibility to alcohol-induced chronic liver injury and hepatic insulin resistance. *Gastroenterol Res Pract* 2010.

Dong Y L, Gangula P R, Fang L & Yallampalli C. (1996). Differential expression of cyclooxygenase-1 and -2 proteins in rat uterus and cervix during the estrous cycle, pregnancy, labor and in myometrial cells. *Prostaglandins* 52, 13-34.

Faraji J, Sutherland R J & Metz G A. (2011). Stress precipitates functional deficits following striatal silent stroke: A synergistic effect. *Exp Neurol* 232, 251-260.

Fuchs A R. (1978). Hormonal control of myometrial function during pregnancy and parturition. *Acta endocrinologica* 221, 1-70.

Fuchs A R, Periyasamy S & Soloff M S. (1983). Systemic and local regulation of oxytocin receptors in the rat uterus, and their functional significance. *Can J Biochem Cell Biol* 61, 615-624.

Garfield R E, Kannan M S & Daniel E E. (1980). Gap junction formation in myometrium: control by estrogens, progesterone, and prostaglandins. *Am J Physiol* 238, C81-89.

Garfield R E, Sims S & Daniel E E. (1977). Gap junctions: their presence and necessity in myometrium during parturition. *Science* 198, 958-960.

Gomez-Lopez N, Estrada-Gutierrez G, Jimenez-Zamudio L, Vega-Sanchez R & Vadillo-Ortega F. (2009). Fetal membranes exhibit selective leukocyte chemotaxic activity during human labor. *J Reprod Immunol* 80, 122-131.

Gomez-Lopez N, Guilbert L J & Olson D M. (2010a). Invasion of the leukocytes into the fetal-maternal interface during pregnancy. *Journal of leukocyte biology* 88, 625-633.

Gomez-Lopez N, Laresgoiti-Servitje E, Olson D M, Estrada-Gutierrez G & Vadillo-Ortega F. (2010b). The Role of Chemokines in Term and Premature Rupture of the Fetal Membranes: A Review. *Biology of reproduction* 82, 809-814.

Gomez-Lopez N, Vadillo-Perez L, Nessim S, Olson D M & Vadillo-Ortega F. (2011). Choriodecidua and amnion exhibit selective leukocyte chemotaxis during term human labor. *Am J Obstet Gynecol* 204, 364 e369-316.

Gorodeski G I, Sheean L A & Utian W H. (1990). Myometrial oxytocin receptors levels in the pregnant rat are higher in distal than in proximal portions of the horn and correlate with disparate oxytocin responsive myometrial contractility in these segments. *Endocrinology* 127, 1136-1143.

Hirsch E, Filipovich Y, Romero R. (2009) Failure of *E. coli* bacteria to induce preterm delivery in the rat. *J Negat Results Biomed.* January 4; 8:1.

Hirst J J, Teixeira F J, Zakar T & Olson D M. (1995). Prostaglandin H synthase-2 expression increases in human gestational tissues with spontaneous labour onset. *Reprod Fertil Dev* 7, 633-637.

Hu X L, Yang Y & Hunt J S. (1992). Differential distribution of interleukin-1 alpha and interleukin-1 beta proteins in human placentas. *J Reprod Immunol* 22, 257-268.

Hunt J S & Pollard J W. (1992). Macrophages in the uterus and placenta. *Curr Top Microbiol Immunol* 181, 39-63.

Kelly R W. (1996). Inflammatory mediators and parturition. *Rev Reprod* 1, 89-96.

Laresgoiti-Servitje E, Gomez-Lopez N & Olson D M. (2010). An immunological insight into the origins of pre-eclampsia. *Hum Reprod Update* 16, 510-524.

Ley K, Laudanna C, Cybulsky M I & Nourshargh S. (2007). Getting to the site of inflammation: the leukocyte adhesion cascade updated. *Nature reviews* 7, 678-689.

Liggins G C. (1981). Cervical ripening as an inflammatory reaction. In *The Cervix in Pregnancy and Labour*, ed. In: Ellwood D, Anderson, A. (Eds.), pp. 1-9. Churchill-Livingstone, Edinburgh.

Luo L, Ibaragi T, Maeda M, Nozawa M, Kasahara T, Sakai M, Sasaki Y, Tanebe K & Saito S. (2000). Interleukin-8 levels and granulocyte counts in cervical mucus during pregnancy. *Am J Reprod Immunol* 43, 78-84.

Lye S J, Ou C—W, Teoh T-G, Erb G, Stevens Y, Casper R, Patel F A & JRG C. (1998). The molecular basis of labour and tocolysis. *Fetal Matern Med Rev* 121-136.

Lye S J, Nicholson B J, Mascarenhas M, MacKenzie L & Petrocelli T. (1993). Increased expression of connexin-43 in the rat myometrium during labor is associated with an increase in the plasma estrogen:progesterone ratio. *Endocrinology* 132, 2380-2386.

Mitchell B F, Zielnik B, Wong S, Roberts C D, Mitchell J M. (2005) Intraperitoneal infusion of proinflammatory cytokines does not cause activation of the rat uterus during late gestation. *Am J Physiol Endocrinol Metab.* October; 289(4):E658-64. Epub 2005 May 3.

Norwitz E R, Robinson J N & Challis J R. (1999). The control of labor. *N Engl J Med* 341, 660-666.

Olson D M, Mijovic J E & Sadowsky D W. (1995). Control of human parturition. *Seminars in perinatology* 19, 52-63.

Osman I, Young A, Ledingham M A, Thomson A J, Jordan F, Greer I A & Norman J E. (2003). Leukocyte density and pro-inflammatory cytokine expression in human fetal membranes, decidua, cervix and myometrium before and during labour at term. *Molecular human reproduction* 9, 41-45.

Paris J J, Brunton P J, Russell J A & Frye C A. (2011). Immune stress in late pregnant rats decreases length of gestation and fecundity, and alters later cognitive and affective behaviour of surviving pre-adolescent offspring. *Stress* 14, 652-664.

Pate J L & Landis Keyes P. (2001). Immune cells in the corpus luteum: friends or foes? *Reproduction* 122, 665-676.

Pfaffl M W. (2001). A new mathematical model for relative quantification in real-time RT-PCR. *Nucleic Acids Res* 29, e45.

Press M F & King W J. (1986). Distribution of peroxidase and granulocytes in the human uterus. *Lab Invest* 54, 188-203.

Pritchard J A, MacDonald P C & Gant N F. (1985). *The placenta and fetal membranes and maternal adaptation to pregnancy*. In Williams' obstetrics, Appleton Century Crofts, Stamford, Conn.

Ramos J G, Varayoud J, Kass L, Rodriguez H, Munoz de Toro M, Montes G S & Luque E H. (2000). Estrogen and progesterone modulation of eosinophilic infiltration of the rat uterine cervix. *Steroids* 65, 409-414.

Risek B, Guthrie S, Kumar N & Gilula N B. (1990). Modulation of gap junction transcript and protein expression during pregnancy in the rat. *The Journal of cell biology* 110, 269-282.

Shaikh A A. (1971). Estrone and estradiol levels in the ovarian venous blood from rats during the estrous cycle and pregnancy. *Biology of reproduction* 5, 297-307.

Shynlova O, Tsui P, Dorogin A & Lye S J. (2008). Monocyte chemoattractant protein-1 (CCL-2) integrates mechanical and endocrine signals that mediate term and preterm labor. *J Immunol* 181, 1470-1479.

Soloff M S, Alexandrova M & Fernstrom M J. (1979). Oxytocin receptors: triggers for parturition and lactation? *Science* 204, 1313-1315.

Springer T A. (1995). Traffic signals on endothelium for lymphocyte recirculation and leukocyte emigration. *Annual review of physiology* 57, 827-872.

Sugimoto Y, Yamasaki A, Segi E, Tsuboi K, Aze Y, Nishimura T, Oida H, Yoshida N, Tanaka T, Katsuyama M, Hasumoto K, Murata T, Hirata M, Ushikubi F, Negishi M, Ichikawa A & Narumiya S. (1997). Failure of parturition in mice lacking the prostaglandin F receptor. *Science* 277, 681-683.

Tamassia N, Le Moigne V, Calzetti F, Donini M, Gasperini S, Ear T, Cloutier A, Martinez F O, Fabbri M, Locati M, Mantovani A, McDonald P P & Cassatella M A. (2007). The MyD88-independent pathway is not mobilized in human neutrophils stimulated via TLR4. *J Immunol* 178, 7344-7356.

Timmons B, Akins M & Mahendroo M. (2010). Cervical remodeling during pregnancy and parturition. *Trends Endocrinol Metab* 21, 353-361.

Vane J R, Bakhle Y S & Botting R M. (1998). Cyclooxygenases 1 and 2. *Annual review of pharmacology and toxicology* 38, 97-120.

Yellon S M, Mackler A M & Kirby M A. (2003). The role of leukocyte traffic and activation in parturition. *J Soc Gynecol Investig* 10, 323-338.

Yuan M, Jordan F, McInnes I B, Harnett M M & Norman J E. (2009). Leukocytes are primed in peripheral blood for activation during term and preterm labour. *Molecular human reproduction* 15, 713-724.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The embodiments of the invention in which an exclusive property or privilege is claimed are defined as follows:

1. A method for determining the likelihood of a pregnant subject developing a disorder associated with pregnancy, comprising: obtaining peripheral leukocytes from said pregnant subject prior to about week 37 of pregnancy; and determining a chemotactic activity of said leukocytes, wherein an increased likelihood of developing said disorder associated with pregnancy is indicated when said chemotactic activity of said leukocytes is at a level characteristic of a full term pregnancy, wherein determining said chemotactic activity comprises measuring migration of said leukocytes towards a chemoattractant, wherein said chemoattractant is a choriodecidua extract, a full thickness fetal membrane extract, a placental extract, or a cervical extract, wherein each said extract is obtained from a full term pregnancy subject.

2. The method of claim 1, wherein said disorder associated with pregnancy is preterm delivery, preeclampsia, preterm premature rupture of membranes, or placental abruption.

3. The method of claim 1, wherein said uterine extract comprises an upper uterine extract, a middle uterine extract, a lower uterine extract, or a cervical extract.

4. A method for determining the likelihood of a pregnant subject undergoing preterm delivery, comprising: obtaining peripheral leukocytes from said pregnant subject prior to about week 37 of pregnancy; and determining a chemotactic activity of said leukocytes, wherein an increased likelihood of preterm delivery is indicated when said chemotactic activity of said leukocytes is at a level characteristic of a full term pregnancy, wherein determining said chemotactic activity comprises measuring migration of said leukocytes towards a chemoattractant, wherein said chemoattractant is a choriodecidua extract, a full thickness fetal membrane extract, a uterine extract, a placental extract, or a cervical extract, wherein each said extract is obtained from a full term pregnancy subject.

5. The method of claim 4, wherein said leukocyte is a granulocyte, T-lymphocyte, monocyte, macrophage, NK cell, or B-lymphocyte.

6. The method of claim 4, wherein said subject is a human.

* * * * *